(12) United States Patent
Barthelemy et al.

(10) Patent No.: US 9,707,250 B2
(45) Date of Patent: Jul. 18, 2017

(54) HYDROPHOBICALLY MODIFIED ANTISENSE OLIGONUCLEOTIDES COMPRISING A TRIPLE ALKYL CHAIN

(71) Applicants: INSTITUT NATIONAL DE LA SANTE ET DE LA RECHERCHE MEDICALE (INSERM), Paris (FR); UNIVERSITE DE BORDEAUX, Bordeaux (FR); UNIVERSITE D'AIX-MARSEILLE, Marseilles (FR); INSTITUT JEAN PAOLI & IRENE CALMETTES, Marseilles (FR); CENTRE NATIONAL DE LA RECHERCHE SCIENTIFIQUE, Paris (FR)

(72) Inventors: Philippe Barthelemy, Bordeaux (FR); Khalid Oumzil, Bordeaux (FR); Arnaud Gissot, Bordeaux (FR); Palma Rocchi, Marseilles (FR); Julie Acunzo, Marseilles (FR)

(73) Assignees: INSTITUT NATIONAL DE LA SANTE ET DE LA RECHERCHE MEDICALE (INSERM), Paris (FR); UNIVERSITÉ DE BORDEAUX, Paris (FR); Université d' Aix-Marseille, Marseilles (FR); Institut Jean Paoli & Irene Calmettes, Marseilles (FR); Centre Régional de Lutte Contre le Cancer, Marseilles (FR); CENTRE NATIONAL DE LA RECHERCHE SCIENTIFIQUE (C.N.R.S), Paris (FR)

( * ) Notice: Subject to any disclaimer, the term of this patent is extended or adjusted under 35 U.S.C. 154(b) by 0 days.

(21) Appl. No.: 14/895,344

(22) PCT Filed: Jun. 5, 2014

(86) PCT No.: PCT/EP2014/061762
§ 371 (c)(1),
(2) Date: Dec. 2, 2015

(87) PCT Pub. No.: WO2014/195432
PCT Pub. Date: Dec. 11, 2014

(65) Prior Publication Data
US 2016/0113957 A1 Apr. 28, 2016

(30) Foreign Application Priority Data

Jun. 5, 2013 (WO) .................. PCT/IB2013/001516

(51) Int. Cl.
A01N 43/04 (2006.01)
A61K 31/70 (2006.01)
A61K 31/713 (2006.01)
A61K 47/48 (2006.01)
C12N 15/11 (2006.01)
C12N 15/113 (2010.01)
A61K 45/06 (2006.01)
A61K 9/127 (2006.01)
A61K 31/337 (2006.01)
A61K 31/712 (2006.01)
A61K 31/7088 (2006.01)

(52) U.S. Cl.
CPC .......... *A61K 31/713* (2013.01); *A61K 9/1271* (2013.01); *A61K 31/337* (2013.01); *A61K 45/06* (2013.01); *A61K 47/488* (2013.01); *A61K 47/48046* (2013.01); *C12N 15/111* (2013.01); *C12N 15/113* (2013.01); *C12N 15/1135* (2013.01); *A61K 31/7088* (2013.01); *A61K 31/712* (2013.01); *C12N 2310/11* (2013.01); *C12N 2310/351* (2013.01); *C12N 2310/3515* (2013.01); *C12N 2330/30* (2013.01)

(58) Field of Classification Search
None
See application file for complete search history.

(56) References Cited

U.S. PATENT DOCUMENTS

2013/0266572 A1* 10/2013 Rocchi ............... C12N 15/1135
424/138.1

FOREIGN PATENT DOCUMENTS

WO 2012/080509 A1 6/2012

OTHER PUBLICATIONS

Pokholenko et al., "Lipid oligonucleotide conjugates as responsive nanomaterials for drug delivery", Journal of Materials Chemistry B, Apr. 26, 2013, p. 5329, vol. 1, No. 3.
Godeau et al., "Lipid-Conjugated Oligonucleotides via "Click Chemistry" Efficiently Inhibit Hepatitis C Virus Translation", Journal of Medicinal Chemistry, Aug. 1, 2008, pp. 4374-4376, vol. 51, No. 15.
Chillemi et al., "Oligonucleotides Conjugated to Natural Lipids: Synthesis of Phosphatidyl-Anchored Antisense Oligonucleotides", Bioconjugate Chemistry, Apr. 17, 2013, pp. 648-657, vol. 24, No. 4.
Gissot et al., "Nucleoside, nucleotide and oligonucleotide based amphiphiles: a successful marriage if nucleic acids with lipids", Organic & Biomolecular Chemistry, Jan. 1, 2008, p. 1324, vol. 6, No. 8.
Patwa et al., "Hybrid lipid oligonucleotide conjugates: synthesis, self-assemblies, and biomedical applications", Chemical Society Reviews, Jan. 1, 2011, p. 5844, vol. 40, No. 12.

(Continued)

*Primary Examiner* — Patrick Lewis
(74) *Attorney, Agent, or Firm* — Whitham, Curtis & Cook

(57) ABSTRACT

The present invention concerns an oligonucleotide modified by substitution at the 3' or the 5' end by a moiety comprising at least three saturated or unsaturated, linear or branched hydrocarbon chains comprising from 2 to 30 carbon atoms, and the use therefore as a medicament, in particular for use for treating cancer.

19 Claims, 5 Drawing Sheets

(56) References Cited

OTHER PUBLICATIONS

M. Muthiah, "Oligonucleotide conjugates as potential antisense drugs with improved uptake, biodistribution, targeted delivery, and mechanisms of action", Antisense & Nucleic Acid Drug Development, Apr. 1, 2002, pp. 103-128, vol. 12, No. 2.

Stein et al., "Efficient gene silencing by delivery of locked nucleic acid antisense oligonucleotides, unassisted by transfection reagents", Nucleic Acids Research, Jan. 1, 2010, p. e3, vol. 38, No. 1.

\* cited by examiner

SEQUENCE LISTING

<160> NUMBER OF SEQ ID NOS: 33

<210> SEQ ID NO 1
<211> LENGTH: 172
<212> TYPE: PRT
<213> ORGANISM: Homo sapiens

<400> SEQUENCE: 1

Met Ile Ile Tyr Arg Asp Leu Ile Ser His Asp Glu Met Phe Ser Asp
1               5                   10                  15

Ile Tyr Lys Ile Arg Glu Ile Ala Asp Gly Leu Cys Leu Glu Val Glu
            20                  25                  30

Gly Lys Met Val Ser Arg Thr Glu Gly Asn Ile Asp Asp Ser Leu Ile
        35                  40                  45

Gly Gly Asn Ala Ser Ala Glu Gly Pro Glu Gly Glu Gly Thr Glu Ser
    50                  55                  60

Thr Val Ile Thr Gly Val Asp Ile Val Met Asn His His Leu Gln Glu
65                  70                  75                  80

Thr Ser Phe Thr Lys Glu Ala Tyr Lys Lys Tyr Ile Lys Asp Tyr Met
                85                  90                  95

Lys Ser Ile Lys Gly Lys Leu Glu Glu Gln Arg Pro Glu Arg Val Lys
            100                 105                 110

Pro Phe Met Thr Gly Ala Ala Glu Gln Ile Lys His Ile Leu Ala Asn
        115                 120                 125

Phe Lys Asn Tyr Gln Phe Phe Ile Gly Glu Asn Met Asn Pro Asp Gly
    130                 135                 140

Met Val Ala Leu Leu Asp Tyr Arg Glu Asp Gly Val Thr Pro Tyr Met
145                 150                 155                 160

Ile Phe Phe Lys Asp Gly Leu Glu Met Glu Lys Cys
                165                 170

<210> SEQ ID NO 2
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 2
accaatgagc gagtcatcaa                                                    20

<210> SEQ ID NO 3
<211> LENGTH: 21
<212> TYPE: RNA
<213> ORGANISM: Artificial Sequence
<220> FEATURE:
<223> OTHER INFORMATION: Synthetic siRNA targeting TCTP

<400> SEQUENCE: 3
aacccguccg cgaucucccg g                                                  21

<210> SEQ ID NO 4
<211> LENGTH: 19
<212> TYPE: DNA
<213> ORGANISM: Artificial Sequence
<220> FEATURE:
<223> OTHER INFORMATION: Synthetic scrambled oligonucleotide

<400> SEQUENCE: 4
cgtgtaggta cggcagatc                                                     19

```
<210> SEQ ID NO 5
<211> LENGTH: 829
<212> TYPE: DNA
<213> ORGANISM: Homo sapiens
<220> FEATURE:
<221> NAME/KEY: misc_feature
<222> LOCATION: (153)..(173)
<223> OTHER INFORMATION: Region targeted by the siRNA of SEQ ID NO: 3
<220> FEATURE:
<221> NAME/KEY: misc_feature
<222> LOCATION: (221)..(240)
<223> OTHER INFORMATION: Region targeted by the antisense
      oligonucleotide of SEQ ID NO: 2

<400> SEQUENCE: 5 cccccgagc gccgctccgg ctgcaccgcg ctcgctccga gtttcaggct cgtgctaagc      60
tagcgccgtc gtcgtctccc ttcagtcgcc atcatgatta tctaccggga cctcatcagc    120
cacgatgaga tgttctccga catctacaag atccgggaga tcgcggacgg gttgtgcctg    180
gaggtggagg ggaagatggt cagtaggaca gaaggtaaca ttgatgactc gctcattggt    240
ggaaatgcct ccgctgaagg ccccgagggc gaaggtaccg aaagcacagt aatcactggt    300
gtcgatattg tcatgaacca tcacctgcag gaaacaagtt tcacaaaaga agcctacaag    360
aagtacatca agattacat gaaatcaatc aaagggaaac ttgaagaaca gagaccagaa     420
agagtaaaac cttttatgac aggggctgca gaacaaatca agcacatcct tgctaatttc    480
aaaaactacc agttctttat tggtgaaaac atgaatccag atggcatggt tgctctattg    540
gactaccgtg aggatggtgt gacccccatat atgattttct ttaaggatgg tttagaaatg   600
gaaaaatgtt aacaaatgtg gcaattattt tggatctatc acctgtcatc ataactggct    660
tctgcttgtc atccacacaa caccaggact taagacaaat gggactgatg tcatcttgag    720
ctcttcattt attttgactg tgatttattt ggagtggagg cattgttttt aagaaaaaca    780
tgtcatgtag gttgtctaaa aataaaatgc atttaaactc atttgagag                829

<210> SEQ ID NO 6
<211> LENGTH: 20
<212> TYPE: DNA
<213> ORGANISM: Artificial Sequence
<220> FEATURE:
<223> OTHER INFORMATION: Synthetic region targeted by the antisense
      oligonucleotide of SEQ ID NO: 2

<400> SEQUENCE: 6
aacttgtttc ctgcaggtga                                                 20

<210> SEQ ID NO 7
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 7
tggttcatga caatatcgac                                                 20

<210> SEQ ID NO 8
<211> LENGTH: 20
<212> TYPE: DNA
<213> ORGANISM: Artificial Sequence
<220> FEATURE:
<223> OTHER INFORMATION: Synthetic antisense oligonucleotide targeting
```

```
                                  TCTP

<400> SEQUENCE: 8
taatcatgat ggcgactgaa                                                 20

<210> SEQ ID NO 9
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 9
gctgatgagg tcccggtaga                                                 20

<210> SEQ ID NO 10
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 10
tcggagaaca tctcatcgtg                                                 20

<210> SEQ ID NO 11
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 11
caggcacaac ccgtccgcga                                                 20

<210> SEQ ID NO 12
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 12
accatcttcc cctccacctc                                                 20

<210> SEQ ID NO 13
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 13
tgttaccttc tgtcctactg                                                 20

<210> SEQ ID NO 14
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP
```

-continued

<400> SEQUENCE: 14
ccttcagcgg aggcatttcc                                               20

<210> SEQ ID NO 15
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 15
cagtaccttc gccctcgggg                                               20

<210> SEQ ID NO 16
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 16
accagtgatt actgtgcttt                                               20

<210> SEQ ID NO 17
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 17
cttgtaggct tcttttgtga                                               20

<210> SEQ ID NO 18
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 18
atgtaatctt tgatgtactt                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 19
gtttcccttt gattgatttc                                               20

<210> SEQ ID NO 20
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 20
ttctggtctc tgttcttcaa                                          20

<210> SEQ ID NO 21
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 21
ataaagaact ggtagttttt                                          20

<210> SEQ ID NO 22
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 22
ctggattcat gttttcacca                                          20

<210> SEQ ID NO 23
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 23
caatagagca accatgccat                                          20

<210> SEQ ID NO 24
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 24
acaccatcct cacggtagtc                                          20

<210> SEQ ID NO 25
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 25
agaaaatcat atatggggtc                                          20

<210> SEQ ID NO 26
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 26
catttctaaa ccatccttaa                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 27
ttaacatttc tccatttcta                                              20

<210> SEQ ID NO 28
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 28
tctcccggat cttgtagatg                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 29
gtcataaaag gttttactct                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 30
tgatttgttc tgcagcccct                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic antisense oligonucleotide targeting
      TCTP

<400> SEQUENCE: 31
gaaattagca aggatgtgct                                              20

<210> SEQ ID NO 32
<211> LENGTH: 15
<212> TYPE: DNA
<213> ORGANISM: Artificial Sequence
<220> FEATURE:
<223> OTHER INFORMATION: Synthetic dA15

<400> SEQUENCE: 32
aaaaaaaaaa aaaaa                                                   15

```
<210> SEQ ID NO 33
<211> LENGTH: 15
<212> TYPE: DNA
<213> ORGANISM: Artificial Sequence
<220> FEATURE:
<223> OTHER INFORMATION: Synthetic dT15

<400> SEQUENCE: 33
tttttttttt ttttt                                                    15
```

HYDROPHOBICALLY MODIFIED ANTISENSE OLIGONUCLEOTIDES COMPRISING A TRIPLE ALKYL CHAIN

The present invention concerns hydrophobically modified oligonucleotides, their process of manufacture, pharmaceutical compositions comprising said modified oligonucleotides, and their use as vehicles for the administration of drugs.

There is currently substantial interest in the use of nucleic acids for modifying gene expression for therapeutic purposes. The use of oligonucleotide (ON) analogues as potential therapeutic agents for modulating the expression of specific genes has shown promise for different classes of molecules, including aptamers, triplex-forming oligonucleotides, antisense oligonucleotides (ASO), small interfering RNAs (siRNAs) and antagomirs. However, one major barrier in the broad utilization of ON analogues as clinical drugs is their reduced ability to transverse cell membranes.

Cellular uptake and localization of ONs are crucial problems for their effects on the genetic expressions. Most approaches for their cellular delivery involve cationic lipophilic carriers and/or polymers. While such synthetic carriers can be exceptionally effective for delivering plasmid DNA into the cytoplasm of cells, most are of limited utility because of their toxicity to cells and poor efficiency in the case of ONs. Alternatively, a lipophilic moiety has been covalently tethered to the ON structures with the aim of improving cellular uptake and antisense activity. Lipid conjugated ONs (LONs) feature an oligonucleotide sequence as the polar head and at least one lipid moiety inserted either at the 3'- or 5'-end of the oligonucleotide or within the sequence. Interestingly, LONs self assemble to give aggregates such as micelles and vesicles. The appended lipidic segment of LONs brings about new properties to these surfactants like enhanced antisense activities, tagging of vesicles or lipid bilayers, and biological membranes. LONs have also been successfully implemented in original detection schemes for nucleic acids, and as biotechnological tools.

However, the LONs developed so far have the drawback of bearing non-cleavable lipid moieties which might affect the inhibitory efficiency of the ONs, once internalized in the targeted cells.

There is therefore still a need for alternative modified antisense ONs with (i) a high cellular uptake, (ii) a prolonged half-life on plasma, and (iii) a high efficiency of gene silencing in vivo.

The present invention arises from the unexpected finding by the inventors that an antisense oligonucleotide modified by substitution at the 5' or 3' end by a moiety comprising three hydrocarbon chains, which can be metabolized, had an increased inhibitory power in vivo compared to the same ASO bearing other 5' modifications, even in the absence of any transfection reagent.

Additionally, the present inventors demonstrated that these LASOs were capable of aggregating thereby creating a lipophilic core or reservoir, which could be used for the loading of hydrophobic drugs, such as Paclitaxel, and that this drug loading could be modulated via the hybridization of the complementary ASO sequence. Such LASOs aggregates can therefore be used to specifically trigger the release of a drug in vivo.

The present invention therefore concerns an oligonucleotide modified by substitution at the 3' or the 5' end by a moiety comprising at least three saturated or unsaturated, linear or branched hydrocarbon chains comprising from 2 to 30 carbon atoms.

The present invention also relates to a process of manufacture of a modified oligonucleotide as defined herein, comprising the steps of:
(i) synthesizing the oligonucleotide;
(ii) modifying the oligonucleotide by reaction with a suitable reactant comprising a moiety having at least three saturated or unsaturated, linear or branched hydrocarbon chains comprising from 2 to 30 carbon atoms;
(iii) recovering the modified oligonucleotide.

The present invention further concerns a modified antisense oligonucleotide as defined herein for use as a medicament, in particular for use for treating cancer.

The present invention also relates to an aqueous composition comprising modified oligonucleotides as defined herein, wherein the modified oligonucleotides self-assembled into micelles.

The present invention also concerns the use of this aqueous composition as a vehicle.

The present invention also relates to the aqueous composition defined herein, comprising an hydrophobic active principle hosted in said micelles, for use as a medicament, in particular for use for treating cancer.

DETAILED DESCRIPTION OF THE INVENTION

Oligonucleotide

As used herein, the term "oligonucleotide" refers to a nucleic acid sequence, 3'-5' or 5'-3' oriented, which may be single- or double-stranded. The oligonucleotide used in the context of the invention may in particular be DNA or RNA.

The oligonucleotides used in the context of the invention may be further modified, preferably chemically modified, in order to increase the stability and/or therapeutic efficiency of the oligonucleotides in vivo. In particular, the oligonucleotide used in the context of the invention may comprise modified nucleotides.

Chemical modifications may occur at three different sites: (i) at phosphate groups, (ii) on the sugar moiety, and/or (iii) on the entire backbone structure of the oligonucleotide.

For example, the oligonucleotides may be employed as phosphorothioate derivatives (replacement of a non-bridging phosphoryl oxygen atom with a sulfur atom) which have increased resistance to nuclease digestion. 2'-methoxyethyl (MOE) modification (such as the modified backbone commercialized by ISIS Pharmaceuticals) is also effective.

Additionally or alternatively, the oligonucleotides of the invention may comprise completely, partially or in combination, modified nucleotides which are derivatives with substitutions at the 2' position of the sugar, in particular with the following chemical modifications: O-methyl group (2'-O-Me) substitution, 2-methoxyethyl group (2'-O-MOE) substitution, fluoro group (2'-fluoro) substitution, chloro group (2'-Cl) substitution, bromo group (2'-Br) substitution, cyanide group (2'-CN) substitution, trifluoromethyl group (2'-$CF_3$) substitution, $OCF_3$ group (2'-$OCF_3$) substitution, OCN group (2'-OCN) substitution, O-alkyl group (2'-O-alkyl) substitution, S-alkyl group (2'-S-alkyl) substitution, N-alkyl group (2'-N-alkyl) substitution, O-alkenyl group (2'-O-alkenyl) substitution, S-alkenyl group (2'-S-alkenyl) substitution, N-alkenyl group (2'-N-alkenyl) substitution, $SOCH_3$ group (2'-$SOCH_3$) substitution, $SO_2CH_3$ group (2'-$SO_2CH_3$)

substitution, ONO$_2$ group (2'-ONO$_2$) substitution, NO$_2$ group (2'-NO$_2$) substitution, N$_3$ group (2'-N$_3$) substitution and/or NH$_2$ group (2'-NH$_2$) substitution.

Additionally or alternatively, the oligonucleotides of the invention may comprise completely or partially modified nucleotides wherein the ribose moiety is used to produce locked nucleic acid (LNA), in which a covalent bridge is formed between the 2' oxygen and the 4' carbon of the ribose, fixing it in the 3'-endo configuration. These constructs are extremely stable in biological medium, able to activate RNase H and form tight hybrids with complementary RNA and DNA.

Accordingly, in a preferred embodiment, the oligonucleotide used in the context of the invention comprises modified nucleotides selected from the group consisting of LNA, 2'-OMe analogs, 2'-phosphorothioate analogs, 2'-fluoro analogs, 2'-Cl analogs, 2'-Br analogs, 2'-CN analogs, 2'-CF$_3$ analogs, 2'-OCF$_3$ analogs, 2'-OCN analogs, 2'-O-alkyl analogs, 2'-S-alkyl analogs, 2'-N-alkyl analogs, 2'-O-alkenyl analogs, 2'-S-alkenyl analogs, 2'-N-alkenyl analogs, 2'-SOCH$_3$ analogs, 2'-SO$_2$CH$_3$ analogs, 2'-ONO$_2$ analogs, 2'-NO$_2$ analogs, 2'-N$_3$ analogs, 2'-NH$_2$ analogs and combinations thereof. More preferably, the modified nucleotides are selected from the group consisting of LNA, 2'-OMe analogs, 2'-phosphorothioate analogs and 2'-fluoro analogs.

Additionally or alternatively, some nucleobases of the oligonucleotide may be present as desoxyriboses. That modification should only affect the skeleton of the nucleobase, in which the hydroxyl group is absent, but not the side chain of the nucleobase which remains unchanged. Such a modification usually favors recognition of the iRNA by the DICER complex.

The oligonucleotide according to the invention may for example correspond to antisense oligonucleotides or to interfering RNAs (including siRNAs, shRNAs, miRNAs, dsRNAs, and other RNA species that can be cleaved in vivo to form siRNAs), that preferably target mRNAs of interest.

As used herein, an oligonucleotide that "targets" an mRNA refers to an oligonucleotide that is capable of specifically binding to said mRNA. That is to say, the oligonucleotide comprises a sequence that is at least partially complementary, preferably perfectly complementary, to a region of the sequence of said mRNA, said complementarity being sufficient to yield specific binding under intra-cellular conditions.

As immediately apparent to the skilled in the art, by a sequence that is "perfectly complementary to" a second sequence is meant the reverse complement counterpart of the second sequence, either under the form of a DNA molecule or under the form of a RNA molecule. A sequence is "partially complementary to" a second sequence if there are one or more mismatches.

Preferably, the oligonucleotide of the invention targets an mRNA encoding Translationally-Controlled Tumor Protein (TCTP), and is capable of reducing the amount of TCTP in cells.

Nucleic acids that target an mRNA encoding TCTP may be designed by using the sequence of said mRNA as a basis, e.g. using bioinformatic tools. For example, the sequence of SEQ ID NO: 5 can be used as a basis for designing nucleic acids that target an mRNA encoding TCTP.

Preferably, the oligonucleotides according to the invention are capable of reducing the amount of TCTP in cells, e.g. in cancerous cells such as LNCaP or PC3 cells. Methods for determining whether an oligonucleotide is capable of reducing the amount of TCTP in cells are known to the skilled in the art. This may for example be done by analyzing TCTP protein expression by Western blot, and by comparing TCTP protein expression in the presence and in the absence of the oligonucleotide to be tested.

The oligonucleotides according to the invention typically have a length of from 12 to 50 nucleotides, e.g. 12 to 35 nucleotides, from 12 to 30, from 12 to 25, from 12 to 22, from 15 to 35, from 15 to 30, from 15 to 25, from 15 to 22, from 18 to 22, or about 19, 20 or 21 nucleotides.

The oligonucleotides according to the invention may for example comprise or consist of 12 to 50 consecutive nucleotides, e.g. 12 to 35, from 12 to 30, from 12 to 25, from 12 to 22, from 15 to 35, from 15 to 30, from 15 to 25, from 15 to 22, from 18 to 22, or about 19, 20 or 21 consecutive nucleotides of a sequence complementary to the mRNA of SEQ ID NO: 5.

In particular, the inventors have identified thirteen oligonucleotides targeting an mRNA encoding TCTP that are very efficient in reducing the amount of TCTP in cells. These oligonucleotides target the regions consisting of nucleotides 153 to 173 of SEQ ID NO: 5, nucleotides 220 to 240 of SEQ ID NO: 5, nucleotides 300 to 320 of SEQ ID NO: 5, and nucleotides 320 to 340 of SEQ ID NO: 5, respectively. All of these oligonucleotides target the translated region of the TCTP mRNA (which extends from nucleotide 94 to 612 of SEQ ID NO: 5).

Therefore, the oligonucleotides according to the invention preferably target a sequence overlapping with nucleotides 153 to 173, or with nucleotides 221 to 240 or with nucleotides 300 to 340 of SEQ ID NO: 5, said oligonucleotide being a DNA or a RNA. Such an oligonucleotide may for example target:

a sequence consisting of nucleotides 153 to 173 or of nucleotides 221 to 240 or of nucleotides 300 to 320, or of nucleotides 320 to 340 of SEQ ID NO: 5, or a sequence comprised within nucleotides 153 to 173 or within nucleotides 221 to 240, or within nucleotides 300 to 320, or within nucleotides 320 to 340 of SEQ ID NO: 5, or a sequence partially comprised within nucleotides 153 to 173 or within nucleotides 221 to 240, or within nucleotides 300 to 320, or within nucleotides 320 to 340 of SEQ ID NO: 5.

The oligonucleotides according to the invention may for example comprise a fragment of at least 10 consecutive nucleotides of a sequence selected from the group consisting of SEQ ID NO: 2 (5'-ACCAATGAGCGAGTCATCAA-3'), SEQ ID NO: 3 (5'-AACCCGUCCGCGAUCUCCCGG-3'), SEQ ID NO: 6 (5'-AACTTGTTTCCTGCAGGTGA-3'), SEQ ID NO: 7 (5'-TGGTTCATGACAATATCGAC-3'), SEQ ID NO: 8 (5'-TAATCATGATGGCGACTGAA-3'), SEQ ID NO: 16 (5'-ACCAGTGATTACTGTGCTTT-3'), SEQ ID NO: 17 (5'-CTTGTAGGCTTCTTTTGTGA-3'), SEQ ID NO: 18 (5'-ATGTAATCTTTGATGTACTT-3'), SEQ ID NO: 19 (5'-GTTTCCCTTTGATTGATTTC-3'), SEQ ID NO: 20 (5'-TTCTGGTCTCTGTTCTTCAA-3'), SEQ ID NO: 25 (5'-AGAAAATCATATATGGGGTC-3'), SEQ ID NO: 27 (5'-TTAACATTTCTCCATTTCTA-3'), SEQ ID NO: 29 (5'-GTCATAAAAGGTTTTACTCT-3') and SEQ ID NO: 31 (5'-GAAATTAGCAAGGATGTGCT-3'). More preferably, the oligonucleotides comprise a sequence selected from the group consisting of SEQ ID NO: 2, SEQ ID NO: 3, SEQ ID NO: 6, SEQ ID NO: 7, SEQ ID NO: 8, SEQ ID NO: 16, SEQ ID NO: 17, SEQ ID NO: 18, SEQ ID NO: 19, SEQ ID NO: 20, SEQ ID NO: 25, SEQ ID NO: 27, SEQ ID NO: 29 and SEQ ID NO: 31. The oligonucleotides according to the invention may for example comprise a fragment of at least 10 consecutive nucleotides of a sequence of SEQ ID NO: 2 or of a sequence of SEQ ID NO: 6, or of a sequence of SEQ ID NO: 7, or of a sequence of SEQ ID NO: 3. Most preferably, they comprise a sequence of SEQ ID NO: 2, or a sequence of SEQ ID NO: 6, or a sequence of SEQ ID NO: 7 or a sequence of SEQ ID NO: 3. Still preferably, the oligonucleotides according to the invention comprise a fragment of at least 10 consecutive nucleotides of a sequence of SEQ ID NO: 6. Most preferably, they comprise a sequence of SEQ ID NO: 6.

In a preferred embodiment according to the invention, the oligonucleotide is an antisense oligonucleotide.

As used herein, the term "antisense oligonucleotide" refers to a single stranded DNA or RNA with complementary sequence to its target mRNA, and which binds its target mRNA thereby preventing protein translation either by steric hindrance of the ribosomal machinery or induction of mRNA degradation by ribonuclease H.

The antisense oligonucleotide may be a DNA or a RNA molecule.

Said antisense oligonucleotide may for example comprise or consist of a fragment of at least 10, 12, 15, 18 or 20 consecutive nucleotides of a sequence selected from the group consisting of SEQ ID NO: 2 (5'-ACCAATGAGC-GAGTCATCAA-3'), SEQ ID NO: 6 (5'-AACTTGTTTC-CTGCAGGTGA-3'), SEQ ID NO: 7 (5'-TGGTTCAT-GACAATATCGAC-3'), SEQ ID NO: 8 (5'-TAATCATGATGGCGACTGAA-3'), SEQ ID NO: 16 (5'-ACCAGTGATTACTGTGCTTT-3'), SEQ ID NO: 17 (5'-CTTGTAGGCTTCTTTTGTGA-3'), SEQ ID NO: 18 (5'-ATGTAATCTTTGATGTACTT-3'), SEQ ID NO: 19 (5'-GTTTCCCTTTGATTGATTTC-3'), SEQ ID NO: 20 (5'-TTCTGGTCTCTGTTCTTCAA-3'), SEQ ID NO: 25 (5'-AGAAAATCATATATGGGGTC-3'), SEQ ID NO: 27 (5'-TTAACATTTCTCCATTTCTA-3'), SEQ ID NO: 29 (5'-GTCATAAAAGGTTTTACTCT-3') and SEQ ID NO: 31 (5'-GAAATTAGCAAGGATGTGCT-3'), preferably of a sequence SEQ ID NO: 2 (5'-ACCAATGAGCGAGTCAT-CAA-3'), or of a sequence of SEQ ID NO: 6 (5'-AACTT-GTTTCCTGCAGGTGA-3'), or of a sequence of SEQ ID NO: 7 (5'-TGGTTCATGACAATATCGAC-3'). Preferably, it comprises or consists of a sequence selected from the group consisting of SEQ ID NO: 2, SEQ ID NO: 6, SEQ ID NO: 7, SEQ ID NO: 8, SEQ ID NO: 16, SEQ ID NO: 17, SEQ ID NO: 18, SEQ ID NO: 19, SEQ ID NO: 20, SEQ ID NO: 25, SEQ ID NO: 27, SEQ ID NO: 29 and SEQ ID NO: 31, more preferably from the group consisting of SEQ ID NO: 2, SEQ ID NO: 6 and SEQ ID NO: 7. Most preferably, it comprises or consists of the sequence SEQ ID NO: 6.

In another preferred embodiment according to the invention, the oligonucleotide is an interfering RNA (iRNA).

RNA interference is a term initially coined by Fire and co-workers to describe the observation that double-stranded RNA (dsRNA) can block gene expression when it is introduced into worms (Fire et al., 1998, Nature 391:806-811). dsRNA directs gene-specific, post-transcriptional silencing in many organisms, including vertebrates, and has provided a new tool for studying gene function. RNA interference involves mRNA degradation, but many of the biochemical mechanisms underlying this interference are unknown. The use of RNA interference has been further described in Carthew et al. (2001, Current Opinions in Cell Biology, 13:244-248) and in Elbashir et al. (2001, Nature, 411:494-498). The iRNA molecules of the invention are double-stranded or single-stranded RNA, preferably of from about 21 to about 23 nucleotides, which mediate RNA inhibition. That is, the iRNA of the present invention preferably mediate degradation of mRNA encoding TCTP.

The term "iRNA" include double-stranded RNA, single-stranded RNA, isolated RNA (partially purified RNA, essentially pure RNA, synthetic RNA, recombinantly produced RNA), as well as altered RNA that differs from naturally occurring RNA by the addition, deletion, substitution and/or alteration of one or more nucleotides. Such alterations can include addition of non-nucleotide material, such as to the end(s) of the RNA or internally (at one or more nucleotides of the RNA). Nucleotides in the iRNA molecules of the present invention can also comprise non-standard nucleotides, including non-naturally occurring nucleotides or deoxyribonucleotides. Collectively, all such altered iRNA compounds are referred to as analogs or analogs of naturally-occurring RNA. iRNA of the present invention need only be sufficiently similar to natural RNA that it has the ability to mediate RNA interference. As used herein the phrase "mediate RNA Interference" refers to and indicates the ability to distinguish which mRNA are to be affected by the RNA interference machinery or process. RNA that mediates RNA interference interacts with the RNA interference machinery such that it directs the machinery to degrade particular mRNAs or to otherwise reduce the expression of the target protein. In one embodiment, the present invention relates to iRNA molecules that direct cleavage of specific mRNA to which their sequence corresponds. It is not necessary that there be perfect correspondence of the sequences, but the correspondence must be sufficient to enable the iRNA to direct RNA interference inhibition by cleavage or lack of expression of the target mRNA.

The iRNA molecules of the present invention may comprise an RNA portion and some additional portion, for example a deoxyribonucleotide portion. The total number of nucleotides in the RNA molecule is suitably less than 49 in order to be effective mediators of RNA interference. In preferred RNA molecules, the number of nucleotides is 16 to 29, more preferably 18 to 23, and most preferably 21-23.

As indicated above, the term "iRNA" includes but is not limited to siRNAs, shRNAs, miRNAs, dsRNAs, and other RNA species that can be cleaved in vivo to form siRNAs.

A "short interfering RNA" or "siRNA" comprises a RNA duplex (double-stranded region) and can further comprise one or two single-stranded overhangs, 3' or 5' overhangs.

A "short hairpin RNA (shRNA)" refers to a segment of RNA that is complementary to a portion of a target gene (complementary to one or more transcripts of a target gene), and has a stem-loop (hairpin) structure.

"MicroRNAs" or "miRNAs" are endogenously encoded RNAs that are about 22-nucleotide-long, that post-transcriptionally regulate target genes and are generally expressed in a highly tissue-specific or developmental-stage-specific fashion. One can design and express artificial miRNAs based on the features of existing miRNA genes. The miR-30 (microRNA 30) architecture can be used to express miRNAs (or siRNAs) from RNA polymerase II promoter-based expression plasmids (Zeng et al, 2005, Methods enzymol. 392:371-380). In some instances the precursor miRNA molecules may include more than one stem-loop structure. The multiple stem-loop structures may be linked to one another through a linker, such as, for example, a nucleic acid linker, a miRNA flanking sequence, other molecules, or some combination thereof.

In a preferred embodiment according to the invention, the iRNA comprises or consists of a fragment of at least 10, 12, 15 or 18 consecutive nucleotides of a sequence of SEQ ID NO: 3 (5'-AACCCGUCCGCGAUCUCCCGG-3'). Preferably, such a nucleic acid is an iRNA comprising or consisting of a sequence of SEQ ID NO: 3. Most preferably, such a nucleic acid is a siRNA or a shRNA. The sequence of SEQ ID NO: 3 may be modified, and e.g. correspond to a modified sequence of SEQ ID NO: 3 such as a 5'-AACCC-GUCCGCGAUCUCCCdGdG-3' sequence.

The present inventors also demonstrated that modified oligonucleotides comprising an oligonucleotide consisting of an adenine 15-mer of sequence SEQ ID NO: 32 ($dA_{15}$) or of a thymidine 15-mer of sequence SEQ ID NO: 33 ($dT_{15}$) were particularly useful to form micelles capable of encapsulating drugs.

Accordingly, in a preferred embodiment, the oligonucleotide is selected from the group consisting of $dT_{15}$, $dA_{15}$ and an oligonucleotide consisting of the sequence SEQ ID NO: 6.

Lipid Conjugate

The present invention concerns an oligonucleotide, as defined in the section "Oligonucleotide" herein above, modified by substitution at the 3' or the 5' end by a moiety comprising at least three saturated or unsaturated, preferably saturated, linear or branched, preferably linear, hydrocarbon chains comprising from 2 to 30 carbon atoms, preferably from 5 to 20 carbon atoms, more preferably from 10 to 18 carbon atoms.

In a preferred embodiment according to the invention, the modified oligonucleotide is of the general formula (I):

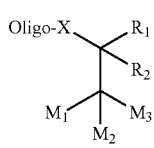

(I)

wherein:

Oligo represents an oligonucleotide sequence which may be oriented 3'-5' or 5'-3', simple and/or double stranded, ADN, ARN, and/or comprise modified nucleotides, in particular an oligonucleotide as defined in the section "Oligonucleotide" herein above;

X represents a divalent linker moiety selected from ether —O—, thio —S—, amino —NH—, and methylene —CH$_2$—;

$R_1$ and $R_2$ may be identical or different and represent:
  (i) a hydrogen atom,
  (ii) a halogen, in particular fluorine atom,
  (iii) a hydroxyl group,
  (iv) an alkyl group comprising from 1 to 12 carbon atoms;

$M_1$, $M_2$ and $M_3$ may be identical or different and represent:
  a saturated or unsaturated, preferably saturated, linear or branched, preferably linear, hydrocarbon chain comprising from 2 to 30 carbon atoms, preferably from 6 to 22 carbon atoms, more preferably from 12 to 20 carbon atoms, which may be substituted by one or more halogen atoms, notably be fluorinated or perfluorinated and/or be interrupted by one or more groups selected from ether —O—, thio —S—, amino —NH—, oxycarbonyl —O—C(O)—, thiocarbamate —O—C(S)—NH—, carbonate —O—C(O)—O—, carbamate —O—C(O)—NH—, phosphate —O—P(O)(O)—O— and phosphonate —P—O(O)(O)— groups; and/or be substituted at the terminal carbon atom by an aliphatic or aromatic, notably benzylic or naphtylic ester or ether group;
  an acyl radical with 2 to 30 carbon atoms, preferably with 6 to 22 carbon atoms, more preferably with 12 to 20 carbon atoms, or
  an acylglycerol, sphingosine or ceramide group.

In the context of the invention, the term "alkyl" refers to a hydrocarbon chain that may be a linear or branched chain, containing the indicated number of carbon atoms. For example, $C_1$-$C_{12}$ alkyl indicates that the group may have from 1 to 12 (inclusive) carbon atoms in it.

In the context of the invention, the term "acyl" refers to an alkylcarbonyl, cycloalkylcarbonyl, arylcarbonyl, heterocyclylcarbonyl or heteroarylcarbonyl substituent.

Preferably, the oligonucleotide sequence "Oligo-" is connected to the divalent linker moiety X via a phosphate moiety —O—P(=O)(O$^-$)—, at its 3' or 5' end, advantageously at its 5' end.

In a preferred embodiment according to the invention, the modified oligonucleotide is of the general formula (I'):

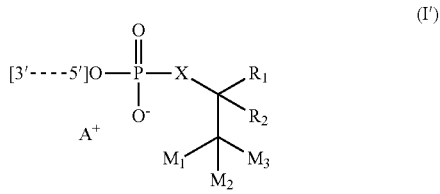

(I')

wherein:

X, $R_1$, $R_2$, $M_1$, $M_2$ and $M_3$ are as defined above in formula (I),

[3'----5'] represents, along with the PO$_3^-$ residue, an oligonucleotide as defined in the section "Oligonucleotide" herein above, and A$^+$ represents a cation, preferably H$^+$, Na$^+$, K$^+$ or NH$_4^+$.

In the formulae (I) and (I'), the divalent linker moiety is preferably ether —O—.

In the formulae (I) and (I'), $R_1$ and $R_2$ are preferably hydrogen atoms.

In a preferred embodiment according to the invention, the modified oligonucleotide is of the formula (I"):

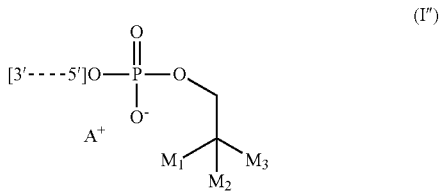

(I")

wherein A$^+$, $M_1$, $M_2$ and $M_3$ are as defined above in formula (I) and [3'----5'] represents, along with the PO$_3^-$ residue, an oligonucleotide as defined in the section "Oligonucleotide" herein above.

In the formulae (I), (I') and (I"), $M_1$, $M_2$ and $M_3$ preferably represent a hydrocarbon chain, preferably a linear hydrocarbon chain, comprising from 6 to 22 carbon atoms, preferably from 12 to 20 carbon atoms, more preferably 18 carbon atoms.

In a preferred embodiment according to the invention, the modified oligonucleotide is of the formula (I'''):

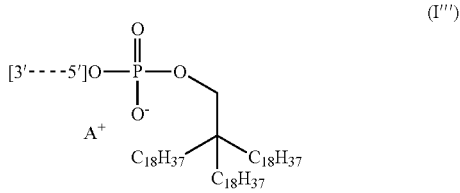

(I''')

wherein $A^+$ is as defined above in formula (I) and [3'----5'] represents, along with the $PO_3^-$ residue, an oligonucleotide as defined in the section "Oligonucleotide" herein above.

In formula (I'''), the chains $-C_{18}H_{37}$ are preferably straight alkyl chains.

Process of Manufacture

The present invention also provides a process of manufacture of a modified oligonucleotide as defined hereabove, comprising the steps of:
(i) synthesizing the oligonucleotide, as defined in the section "Oligonucleotide" herein above;
(ii) modifying the oligonucleotide by reaction with a suitable reactant comprising a moiety having at least three saturated or unsaturated, preferably saturated, linear or branched, preferably linear, hydrocarbon chains comprising from 2 to 30 carbon atoms, preferably from 6 to 22 carbon atoms, more preferably from 12 to 20 carbon atoms;
(iii) recovering the modified oligonucleotide.

Preferably, the suitable reactant of step (ii) comprises a moiety of formula $-C(M_1)(M_2)(M_3)$, wherein $M_1$, $M_2$ and $M_3$ are as defined above in formula (I).

Step (ii) is generally carried out using a coupling methodology.

According to a preferred embodiment of the process of the invention, step (ii) is carried out using the phosphoramidite methodology, which is well-known for the synthesis of oligonucleotides.

Preferably, the reactant used in step (ii) comprises a phosphoramidite group.

A "phosphoramidite group" refers to a monoamide of a phosphite diester moiety, which can be represented as follows $>N-P(-O-)_2$.

The reactant used in step (ii) is preferably of formula (II):

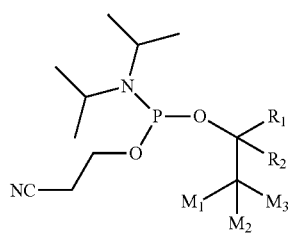

(II)

wherein $R_1$, $R_2$, $M_1$, $M_2$ and $M_3$ are as defined above in formula (I).

When the reactant comprises a phosphoramidite group, step (ii) is generally carried out in the presence of a coupling agent, such as N-benzylthiotetrazole, which activates the phosphoramidite. The oligonucleotide synthesized in step (i), advantageously comprising an OH 5' end, is then added, and the coupling occurs.

The modified oligonucleotide of the invention is then obtained according to usual procedures well-known in the framework of oligonucleotides synthesis.

Aqueous Compositions

The present invention also provides an aqueous composition comprising modified oligonucleotides as defined hereabove, wherein the modified oligonucleotides self-assembled into micelles.

A micelle is an aggregate of surfactant molecules dispersed in a liquid colloid. A typical micelle in aqueous solution forms an aggregate with the hydrophilic "head" regions of the molecules in contact with surrounding aqueous solvent, sequestering the hydrophobic "tail" regions of the molecules in the micelle centre.

The modified oligonucleotides self-assemble into micelles having a core/shell structure, wherein the shell is hydrophilic and is formed of the oligonucleotide parts of the modified oligonucleotides, and wherein the core is lipophilic and is formed of the saturated or unsaturated, linear or branched hydrocarbon chains in $C_2$-$C_{30}$ of the modified oligonucleotides.

The aqueous compositions may comprise up to 50% by weight of modified oligonucleotides, preferably from 0.1% to 40%, in particular from 1% to 20%, and especially from 8% to 15% by weight of modified oligonucleotides.

According to a preferred embodiment, the aqueous composition of the invention further comprises a hydrophobic active principle hosted in said micelles.

Said micelles can be used for the loading of hydrophobic drugs. Loading of such micelles with hydrophobic drug can vary between 2 µM to 2 mM.

The hydrophobic active principle is preferably selected from the group consisting of Paclitaxel, Docetaxel, Vincristine, Vinorelbine, and Abraxane; Tamoxifen, Gonadotrophin-releasing hormone (GnRH) agonists and antagonists, androgen receptor (AR) antagonist, and estrogen receptor (ER) antagonists; Cyclophosphamide, Chlorambucil and Melphalan; Methotrexate, Cytarabine, Fludarabine, 6-Mercaptopurine and 5-Fluorouracil; Doxorubicin, Irinotecan, Platinum derivatives, Cisplatin, Carboplatin, Oxaliplatin; Bicalutamide, Anastrozole, Examestane and Letrozole; Imatinib (Gleevec), Gefitinib and Erlotinib; Rituximab, Trastuzumab (Herceptin) and Gemtuzumab ozogamicin; Interferon-alpha; Tretinoin and Arsenic trioxide; Bevicizumab, Serafinib and Sunitinib.

More preferably, the hydrophobic active principle is Paclitaxel.

Use as Vehicle

The present invention also concerns the use of an aqueous composition as defined in the section "Aqueous composition" hereabove as a vehicle.

As used herein, the term "vehicle" refers to a carrier of a medicinally and/or pharmaceutically active substance.

Preferably, the aqueous composition as defined in the section "Aqueous composition" hereabove is used as a carrier of sparingly hydrosoluble active principle.

Such a vehicle is notably useful for the administration of such active substance by way of intravenous, intraperitoneal, subcutaneous or oral routes, or direct hemoral injection.

The active principle is preferably selected from the group consisting of Paclitaxel, Docetaxel, Vincristine, Vinorelbine, and Abraxane; Tamoxifen, Gonadotrophin-releasing hormone (GnRH) agonists and antagonists, androgen receptor (AR) antagonist, and estrogen receptor (ER) antagonists; Cyclophosphamide, Chlorambucil and Melphalan; Methotrexate, Cytarabine, Fludarabine, 6-Mercaptopurine and 5-Fluorouracil; Doxorubicin, Irinotecan, Platinum derivatives, Cisplatin, Carboplatin, Oxaliplatin; Bicalutamide, Anastrozole, Exemastane and Letrozole; Imatinib (Gleevec), Gefitinib and Erlotinib; Rituximab, Trastuzumab (Herceptin) and Gemtuzumab ozogamicin; Interferon-alpha; Tretinoin and Arsenic trioxide; Bevicizumab, Serafinib and Sunitinib.

More preferably, the hydrophobic active principle is Paclitaxel.

Medical Indications

The inventors have found that the siRNAs and antisense oligonucleotides targeting TCTP inhibit the castration-resistant progression of PC3, LNCaP and C4-2 cells and xenografts and enhance docetaxel and castration-sensitivity. Therefore, the present invention provides a modified oligonucleotide according to the invention as defined hereabove, in particular a modified antisense oligonucleotide according to the invention, in particular an oligonucleotide which targets an mRNA encoding TCTP, for use as a medicament, more particularly for use in the treatment or prevention of cancer, preferably hormone- and/or chemo-resistant cancer. The present invention also provides a modified oligonucleotide according to the invention as defined hereabove, in particular a modified antisense oligonucleotide according to the invention, more particularly an oligonucleotide which targets an mRNA encoding TCTP, for use in restoring sensibility to hormone- and/or chemo-therapy in a patient suffering from cancer.

The invention also provides the use of a modified oligonucleotide according to the invention as defined hereabove, in particular a modified antisense oligonucleotide according to the invention, in particular an oligonucleotide which targets an mRNA encoding TCTP, for the manufacture of a medicament, in particular for the manufacture of a medicament intended to treat or prevent cancer, preferably hormone- and/or chemo-resistant cancer. The invention also provides the use of a modified oligonucleotide according to the invention as defined hereabove, in particular a modified antisense oligonucleotide according to the invention, more particularly an oligonucleotide which targets an mRNA encoding TCTP, for the manufacture of a medicament intended to restore sensibility to hormone- and/or chemo-therapy in a patient suffering from cancer.

The invention also provides a method for treating or preventing cancer and/or for restoring sensibility to hormone- and chemo-therapy comprising the step of administering an effective amount of a modified oligonucleotide according to the invention as defined hereabove, in particular a modified antisense oligonucleotide according to the invention, more particularly an oligonucleotide which targets an mRNA encoding TCTP, to an individual in need thereof.

As used herein, the term "cancer" refers to any type of malignant (i.e. non benign) tumor. The tumor may correspond to a solid malignant tumor, which includes e.g. carcinomas, adenocarcinomas, sarcomas, malignant melanomas, mesotheliomas, blastomas, or to a blood cancer such as leukaemias, lymphomas and myelomas. The cancer may for example correspond to an advanced prostate cancer, a pancreatic cancer, a bladder cancer, an ovarian cancer, a testicular cancer, a cortical adenoma, a colon cancer, a colorectal cancer, a breast cancer or a liver cancer.

Cancers which are preferably treated according to the invention are those wherein TCTP is expressed at higher levels in cancerous cells than in non-cancerous cells of the same tissue type. Exemplary such cancers include without limitation prostate cancer, colon cancer, colorectal cancer, breast cancer, liver cancer, erythroleukemia, gliomas, melanomas, hepatoblastomas and lymphomas.

The oligonucleotides according to the invention, in particular the oligonucleotides which target an mRNA encoding TCTP, are believed to be capable of delaying or preventing the emergence of a resistant hormone-independent phenotype, and to be capable of reversing a resistant hormone-independent phenotype. They are thus particularly suitable for use in the treatment of a hormone-independent cancer or of a hormone-dependent cancer in which hormone-independency is expected to occur. The term "castration" in the expression "castration-resistant" or "castration-independency" according to the invention refers to "hormone" and corresponds to "hormone-resistant" or "hormone-independency". Androgen independency refers to a hormone-independency. Indeed, an androgen-independent prostate cancer (AIPC) is a castration-resistant prostate cancer (CRPC).

Therefore, a preferred embodiment is directed to an oligonucleotide according to the invention as defined hereabove, in particular an oligonucleotide which targets an mRNA encoding TCTP, for use in the treatment or prevention of a hormone-independent or chemo-resistant cancer.

Since the oligonucleotides according to the invention, in particular the oligonucleotides which target an mRNA encoding TCTP, are capable of restoring sensitivity to drugs, they are particularly suitable for use in the treatment of advanced cancers or chemotherapy resistant cancers. The oligonucleotides according to the invention, in particular the oligonucleotides which target an mRNA encoding TCTP, can notably be used as a second line therapy.

The skilled in the art is capable of determining whether a cancer is an "advanced" cancer using well-known classification methods, such as e.g. the grade or the TNM classification. For example, the grade (G1-4) of the cancer cells may be used. More specifically, cancer cells are "low grade" if they appear similar to normal cells, and "high grade" if they appear poorly differentiated. For example, G3 or G4 cancers would be classified as advanced cancers. Additionally or alternatively, the TNM classification may be used. In this classification, T(a,is,(0),1-4) indicates the size or direct extent of the primary tumor, N(0-3) indicates the degree of spread to regional lymph nodes, and M(0/1) indicates the presence of metastasis. For example, a T4/N3/M1 cancer would be classified as an advanced cancer.

Most preferably, the cancer is a prostate cancer, e.g. an advanced prostate cancer and/or an androgen-independent prostate cancer. In a specific embodiment, androgen-dependent prostate cancers can be excluded from the scope of the cancers to be treated in the frame of the present invention.

The inventors have further found that the antisense oligonucleotides according to the invention enhanced the anti-cancer effects of chemotherapy by docetaxel both in vitro and in vivo. In particular, the antagonists according to the invention are believed to be capable of reversing a castration-resistant phenotype and of restoring sensitivity to drugs. Therefore, the oligonucleotides according to the invention, in particular the oligonucleotides which target an mRNA encoding TCTP, can advantageously be used (simultaneously or sequentially) in combination with at least one second anti-cancer agent (e.g. in the frame of a chemotherapy).

In particular, the oligonucleotides according to the invention, in particular the oligonucleotides which target an mRNA encoding TCTP, may be used in the frame of a combination chemotherapy. The oligonucleotides according to the invention, in particular the oligonucleotides which target an mRNA encoding TCTP, may for example be used (simultaneously or sequentially) in combination with at least one of the following anti-cancer agents:

- an antimitotic agent such as Docetaxel, Vincristine, Paclitaxel (Taxol), Vinorelbine, and Abraxane;
- a hormonal therapy drug, such drugs being commonly used in the frame of treatment of hormone-sensitive cancers. Hormonal therapy drugs include, e.g., Tamoxifen, Gonadotrophin-releasing hormone (GnRH) agonists and antagonists, androgen receptor (AR) antagonist, and estrogen receptor (ER) antagonists;
- an alkylating agent such as Cyclophosphamide, Chlorambucil and Melphalan;
- an antimetabolite such as Methotrexate, Cytarabine, Fludarabine, 6-Mercaptopurine and 5-Fluorouracil;
- a topoisomerase inhibitor such as Doxorubicin, Irinotecan, Platinum derivatives, Cisplatin, Carboplatin, Oxaliplatin;
- an aromatase inhibitor such as Bicalutamide, Anastrozole, Examestane and Letrozole;
- a signaling inhibitor such as Imatinib (Gleevec), Gefitinib and Erlotinib;
- a monoclonal antibody such as Rituximab, Trastuzumab (Herceptin) and Gemtuzumab ozogamicin;
- a biologic response modifier such as Interferon-alpha;
- a differentiating agent such as Tretinoin and Arsenic trioxide; and/or
- an agent that block blood vessel formation (antiangiogenic agents) such as Bevicizumab, Serafinib and Sunitinib.

In addition, the method of treating or preventing cancer according to the invention may be associated with a radiation therapy, surgery and/or androgen withdrawal.

Administration of oligonucleotides according to the invention, in particular of oligonucleotides which target an mRNA encoding TCTP, can be carried out using various mechanisms known in the art, including naked administration and administration in pharmaceutically acceptable lipid carriers or nanoparticles. For example, lipid carriers for antisense delivery are disclosed in U.S. Pat. Nos. 5,855,911 and 5,417,978.

They may be for example administered by intravenous, intraperitoneal, subcutaneous or oral routes, or direct local tumor injection.

The oligonucleotide is administered in an "effective amount", i.e. in an amount sufficient to treat or prevent the cancer. It will be appreciated that this amount will vary both with the effectiveness of the oligonucleotides or other therapeutic agent employed, and with the nature of any carrier used. The determination of appropriate amounts for any given composition is within the skill in the art, through standard series of tests designed to assess appropriate therapeutic levels.

In the frame of the present invention, the individual preferably is a human individual. However, the veterinary use of the antagonist according to the present invention is also envisioned. The individual may thus also correspond to a non-human individual, preferably a non-human mammal.

The term "treating" is meant a therapeutic method, i.e. a method aiming at curing, improving the condition and/or extending the lifespan of an individual suffering from the cancer.

By "preventing" is meant a prophylactic method, e.g. aiming at reducing the risk of relapse and/or reducing the risk of appearance of a hormone-independency.

Prostate cancer is one cancer that overexpresses TCTP in advanced cancers, and in particular in cancers that have become castration-resistant. For treatment of prostate cancer, the oligonucleotides according to the invention, in particular the oligonucleotides which target an mRNA encoding TCTP, are suitably administered after initial of androgen withdrawal. Initiation of androgen withdrawal may be accomplished via surgical (removal of both testicles) or medical (drug-induced suppression of testosterone) castration, which is currently indicated for treatment of prostate cancer. Medical castration can be achieved by various regimens, including LHRH agents or antiandrogens (see e.g. Cleave et al., 1999, CMAJ 160:225-232). Intermittent therapy in which reversible androgen withdrawal can be performed as described in Cleave et al. (1998, Eur. Urol. 34: 37-41).

The inhibition of TCTP, in particular of TCTP expression by the oligonucleotides according to the invention, may be transient. For treatment of prostate cancer, the TCTP inhibition should ideally occur coincident with androgen withdrawal. In humans, this means that TCTP inhibition should be effective starting within a day or two of androgen withdrawal (before or after) and extending for about 3 to 6 months. This may require multiple doses to accomplish. It will be appreciated, however, that the period of time may be more prolonged, starting before castration and expending for substantial time afterwards without departing from the scope of the invention.

The present inventors also demonstrated that the modified oligonucleotides of the invention were capable of forming micelles encapsulating hydrophobic active principles, which could release their content when hybridizing with their complementary sequences (FIG. 2). Accordingly, the aqueous compositions of the invention are useful to specifically deliver active principles to cells of interest in order to treat a disease.

The present invention thus also provides an aqueous composition as defined in the section "Aqueous composition" hereabove, for use as a medicament, in particular for use for treating cancer, as defined above.

The present invention also provides the use of an aqueous composition as defined in the section "Aqueous composition" hereabove, for the manufacture of a medicament, in particular intended to treat or prevent cancer, as defined above.

The present invention also provides a method for treating or preventing cancer, as defined above, comprising the step of administering an effective amount of an aqueous composition according to the invention as defined in the section "Aqueous composition" hereabove, to an individual in need thereof.

Pharmaceutical Compositions

The present invention also provides a pharmaceutical composition comprising a modified oligonucleotide according to the invention, and a pharmaceutically acceptable carrier.

Pharmaceutical compositions formulated in a manner suitable for administration of oligonucleotides are known to the skilled in the art. For example, lipidic carriers (in particular liposomes) are particularly suitable pharmaceutically acceptable carriers when administering an oligonucleotide according to the invention.

Non-limiting examples of pharmaceutically acceptable carriers suitable for formulation with the oligonucleotide of the instant invention include: PEG conjugated nucleic acids, phospholipid conjugated nucleic acids, nucleic acids containing lipophilic moieties, phosphorothioates, P-glycoprotein inhibitors (such as Pluronic P85) which can enhance entry of drugs into various tissues, biodegradable polymers (such as poly (DL-lactide-coglycolide) microspheres) for sustained release delivery after implantation, and loaded nanoparticles (such as those made of polybutylcyanoacrylate).

The invention also features pharmaceutical composition comprising surface-modified liposomes containing poly (ethylene glycol) lipids (PEG-modified, branched and unbranched or combinations thereof, or long-circulating liposomes or stealth liposomes). Oligonucleotides of the invention can also comprise covalently attached PEG molecules of various molecular weights. These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al., 1995, Chem. Rev., 95:2601-2627; Ishiwata et al., 1995, Chem. Pharm. Bull., 43:1005-1011). Such liposomes have been shown to accumulate selectively in tumors, presumably by extravasation and capture in the neovascularized target tissues (Lasic et al., 1995, Science, 267:1275-1276; Oku et al., 1995, Biochim. Biophys. Acta, 1238:86-90). The long-circulating liposomes enhance the pharmacokinetics and pharmacodynamics of DNA and RNA. Long-circulating liposomes are also likely to protect drugs from nuclease degradation to a greater extent compared to cationic liposomes.

The pharmaceutical composition of the invention may comprise stabilizers, buffers, and the like. When it is desired to use a liposome delivery mechanism, standard protocols for formation of liposomes can be followed. The compositions of the present invention may be formulated and used as tablets, capsules or elixirs for oral administration, suppositories for rectal administration, sterile solutions or suspensions for injectable administration.

The choice of the formulation ultimately depends on the intended way of administration, such as e.g. an intravenous, intraperitoneal, subcutaneous or oral way of administration, or a local administration via tumor injection. Preferably, the pharmaceutical composition according to the invention is a solution or suspension, e.g. an injectable solution or suspension. It may for example be packaged in dosage unit form.

BRIEF DESCRIPTION OF THE SEQUENCES

SEQ ID NO: 1 shows the sequence of human TCTP protein.
SEQ ID NO: 2, SEQ ID NO: 6, SEQ ID NO: 7 and SEQ ID NO: 8 to SEQ ID NO: 31 show ASO sequences.
SEQ ID NO: 3 shows the sequence of a TCTP siRNA according to the invention.
SEQ ID NO: 4 shows the sequence of a scramble oligonucleotide that has been used as a control.
SEQ ID NO: 5 shows the sequence of a human TCTP mRNA. The regions that are targeted by the TCTP ASO of SEQ ID NO: 2 and by the TCTP siRNA of SEQ ID NO: 3 are indicated.
SEQ ID NO: 32 shows the sequence of $dA_{15}$.
SEQ ID NO: 33 shows the sequence of $dT_{15}$.

The invention will now be described more in detail by way of the examples below and the drawings in annex.

EXAMPLES

Example 1

Figure 1:
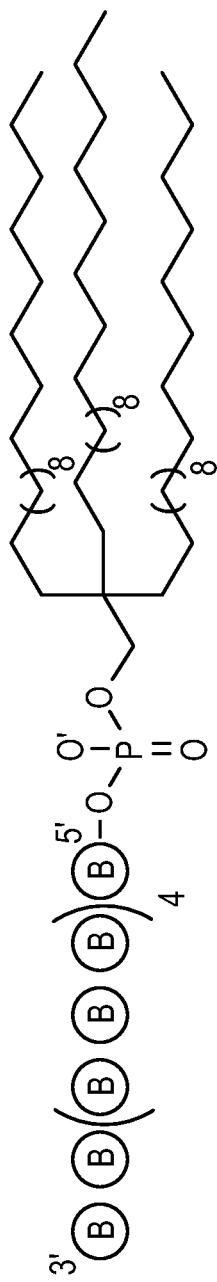
FIG. 1 shows the structural formula of a triple chain LONs according to the present invention.
Figure 2:
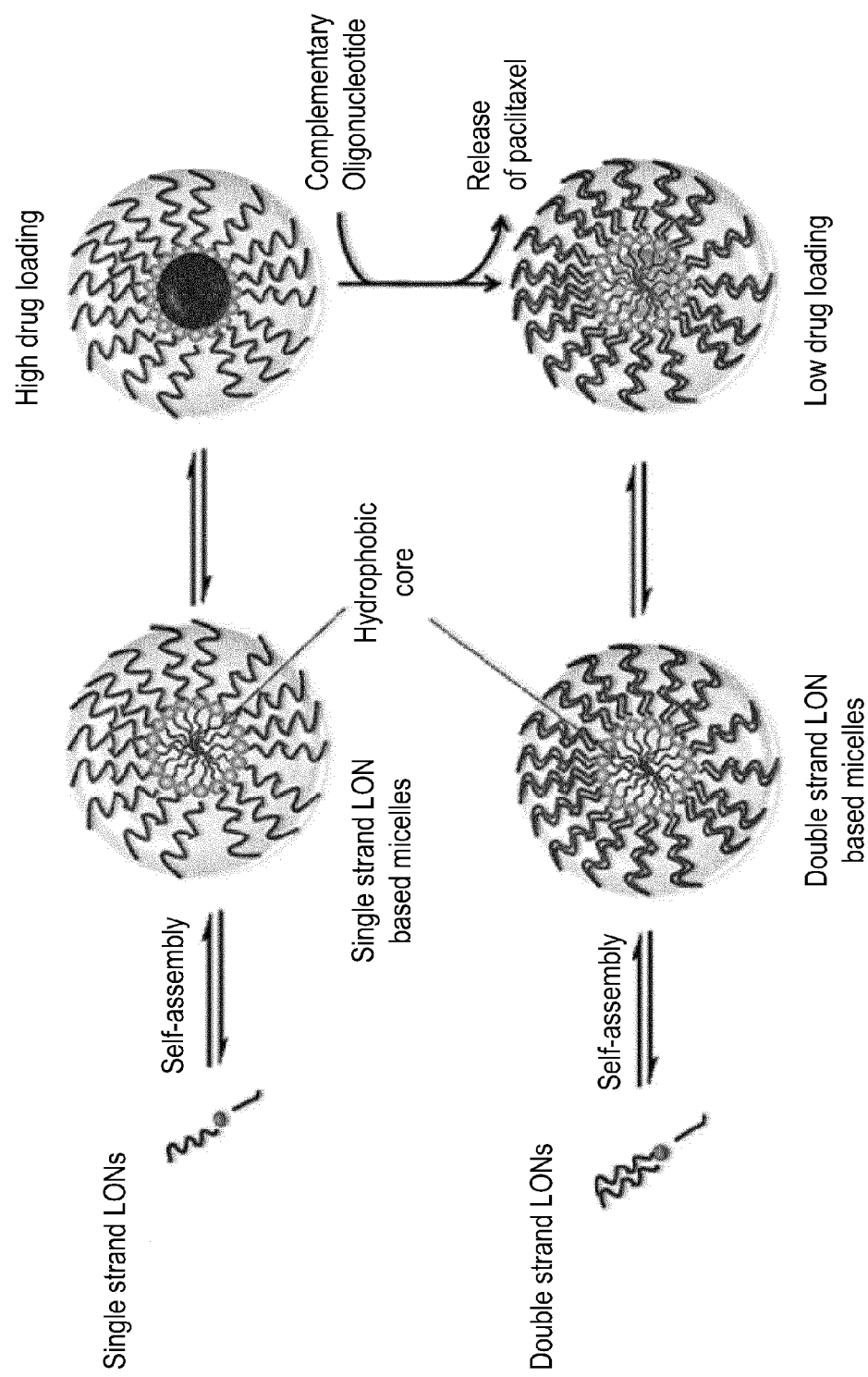
FIG. 2 shows a schematic representation of controlled drug release using single and double strand LON based micelles.

This example describes the synthesis of triple chain phosphoramidite.

The steps required for the synthesis of the phosphoramidite synthon are indicated schematically below.

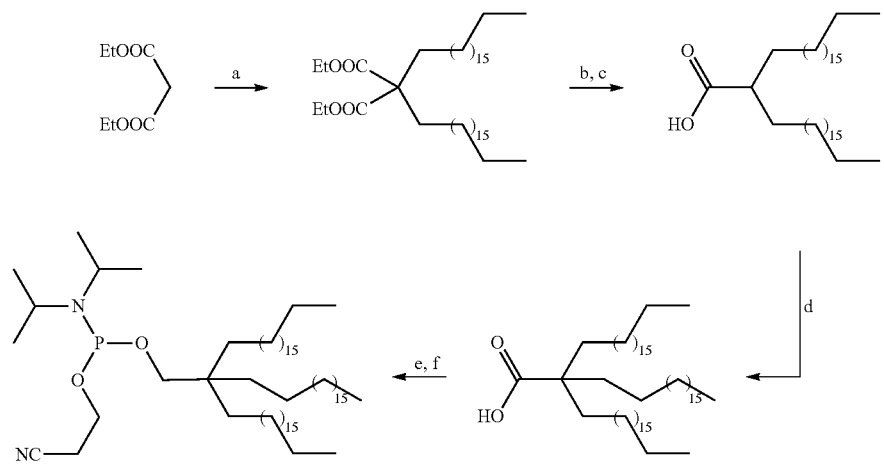

1. Synthesis of 2,2-bis-stearyl acetic acid 2

NaH (60% suspension in oil) (1.517 g, 37.9 mmol) was suspended under argon in 20 mL of dry DMF. Diethyl malonate (1.93 mL, 12.6 mmol) was gradually added at 0° C. After 15 min, a solution of stearyl bromide (8.82 g, 26.5 mmol) in 20 mL of dry THF was added and the resulting mixture stirred at room temperature for 16 h and 4 h at 50° C. MeOH (10 mL) and acetic acid (2 mL) followed by 200 mL of cold water were then added. The aqueous phase was extracted with 3×75 mL of $CH_2Cl_2$. The collected organic layers were washed with brine and dried over $Na_2SO_4$. The resulting solid was recrystallized from iPrOH affording 8.85 g of a white solid.

The obtained 2,2-bis-stearyl diethyl malonate 1 was added to a mixture of aqueous KOH (5 g in 100 mL water) and iPrOH (100 mL). The mixture was heated at 80° C. for 16 h and then diluted with water giving a slurry, which was then neutralized with 50 mL of 47% aqueous $H_2SO_4$. The resulting white solid was filtered and washed with $CH_2Cl_2$ to afford 5.5 g (77% yield) bis-stearyl malonic acid. This acid was almost insoluble in dichloromethane or DMSO at room temperature and slightly more soluble in chloroform. Its solubility in chloroform greatly increases upon heating the solution above 40° C.

Bis-stearyl malonic acid was decarboxylated in boiling decane under inert atmosphere, yielding the desired 2,2-bis-stearyl acetic acid 2, which was purified by chromatography ($CHCl_3$ as eluent) to afford 5.5 g (77% yield) of the desired 2,2-bis-stearyl acetic acid 2.

$^1$H NMR (300 MHz, 320K, $CDCl_3$) δ 2.34 (m, 1H, CHCOOH), 1.63 (m, 3H), 1.50 (m, 3H), 1.48, 1.29 (m, 59H), 0.90 (t, J=6.5 Hz, 6H). $^{13}$C NMR (75 MHz, 320K, $CDCl_3$) δ 177.20, 45.89 (CH), 32.68, 32.11, 29.88, 29.84, 29.81, 29.76, 29.73, 29.68, 29.65, 29.54, 27.65, 22.83, 14.25 ($CH_3$).

2. Synthesis of 2,2,2-tris-stearyl acetic acid 3

LDA (2 M solution, 6.56 mL, 13.12 mmol) was slowly added to 2,2-bis-stearyl acetic acid 2 (3.21 g, 5.68 mmol) in 85 mL dry THF. The mixture was then heated at 50° C. for 2 h to dissolve all remaining solid materials. Stearyl bromide (7.29 g, 21.88 mmol) in 20 mL dry THF was added in portions to the reaction medium and the reaction stirred overnight at room temperature. The solvents were evaporated, 15 mL of aqueous 1M HCl solution was added. The aqueous phase was extracted with hexane followed by $CH_2Cl_2$. The collected organic layers were dried over $Na_2SO_4$. The crude solid was recrystallized from hexane followed by ethyl acetate to afford 3.17 g (68% yield) of pure 3.

$^1$H NMR (300 MHz, $CDCl_3$) δ 1.52 (m, 6H, $CH_2$—C—COOH), 1.25 (m, 97H), 0.88 (t, J=6.4 Hz, 9H). $^{13}$C NMR (75 MHz, $CDCl_3$) δ 184.24, 48.82, 34.33 (broad), 31.97, 30.18 (broad), 29.76, 29.70, 29.53, 29.41, 23.85 (broad), 22.73, 14.15 ($CH_3$).

This product proved especially reluctant to mass analysis using classical protocols (ESI in positive or negative mode, MALDI with ordinary matrices). In contrast, very clean mass spectrum was obtained with a DCTB matrix (trans-2-[3-(4-tert-butylphenyl)-2-methyl-2-propenylidene]malononitrile) doped with $Ag^+$ (or $Na^+$).

Procedure: Samples were dissolved in $CH_2Cl_2$ at 10 mg/ml. The DCTB matrix solution was prepared by dissolving 10 mg in 1 ml of $CH_2Cl_2$. A solution of cationisation agent (AgTFA, 10 mg/ml) was also prepared. The solutions were combined in a 10:1:1 volume ratio of matrix to sample to cationisation agent. One to two microliters of the obtained solution was deposited onto the sample target and vacuum-dried.

MS: $C_{56}H_{112}O_2$ (exact mass=816.87). found 923.80 $[M+Ag]^+$, 1031.72 $[M-H+2Ag]^+$.

3. Synthesis of 2,2,2-tris-stearyl ethanol

LAH (0.45 g, 11.85 mmol) was slowly added in portions to tris-stearyl acetic acid (2 g, 2.45 mmol) in dry THF (15 mL). The reaction mixture was stirred at 65° C. for 12 h. Water followed by aqueous 1M HCl was added. The aqueous phase was extracted with hexane. The collected organic layers were dried over $Na_2SO_4$. The crude was recrystallized from hexane followed by iPrOH to afford 1.40 g (71% yield) of 2,2,2-tris-stearyl ethanol.

$^1$H NMR (300 MHz, $CDCl_3$) δ 3.35 (s, 2H, $CH_2OH$), 1.25 (m, 94H), 1.16 (m, 12H), 0.88 (t, J=6.5 Hz, 9H). $^{13}$C NMR (75 MHz, $CDCl_3$) δ 67.18, 39.47, 33.92, 31.95, 30.63, 29.73, 29.69, 29.39, 22.94, 22.72, 14.16 ($CH_3$).

4. Synthesis of phosphoramidite 4

2,2,2-tris-stearyl ethanol (330 mg, 0.41 mmol) was dried over $P_2O_5$ overnight before use. It was then dissolved in dry $CH_2Cl_2$ (5 mL) containing diisopropylethylamine (0.115 mL, 0.66 mmol). The phosphitylating reagent (0.12 mL, 0.53 mmol) was added to the reaction mixture. The reaction was stirred at room temperature for 3 h and then quenched with saturated aqueous $NaHCO_3$ and extracted with $CH_2Cl_2$. The collected organic layers were washed with water and dried over $Na_2SO_4$. The resulting oil was chromatographed (Hex/EtOAc/TEA 40/2/1) to afford 0.38 g (92% yield) of pure 4 as colorless oil.

RM: this phosphoramidite is quite unstable on silica and must be chromatographed rapidly.

$^1$H NMR (300 MHz, $CDCl_3$) δ 3.81 (m, 2H, $CH_2O$ CNE), 3.58 (m, 2H, iPr), 3.29 (ABX system, $J_{AB}$=9.9 Hz, $J_{AX}$=5.4 Hz, $J_{BX}$=5.3 Hz, 2H, $CH_2O$), 2.62 (t, J=6.6 Hz, 2H, $CH_2CN$), 1.25 (m, 88H), 1.18-1.16 (m, 24H), 0.88 (t, J=6.3 Hz, 9H). $^{13}$C NMR (75 MHz, $CDCl_3$) δ 117.77 (CN) 67.91 (d, J=15.0 Hz), 58.22 (d, J=18.0 Hz), 43.22 (d, J=12.8 Hz), 39.56, 34.34, 32.09, 30.77, 29.88, 29.83, 29.53, 24.77 (d, J=7.5 Hz), 23.04, 22.85, 20.52 (d, J=6.0 Hz), 14.28. $^{31}$P NMR (122 MHz, $CDCl_3$) δ 150.56. MS (ESI, positive mode) $C_{65}H_{131}N_2O_2P$ (exact mass=1002.99). found 1003.1 $[M]^+$ Example 2

This example describes the production of Triple chain polyT 15mer ($^3$LON-$T_{15}$) and Triple chain polyA 15mer ($^3$LON-$A_{15}$)

Prior to use, the phosphoramidite 4 was dried over $P_2O_5$ overnight. It was then dissolved in dry $CH_2Cl_2/CH_3ON$ 3/1 to a 0.1 M concentration. N-benzylthiotetrazole was used for activation of phosphoramidite prior to coupling. The phosphoramidite 4 (200 mL, 0.1 M sol.) was manually coupled last on the solid support with the activator and the phosphoramidite (0.25 mL) for 5 min. Deblocking and detachment from the solid support was achieved using 1 mL of a saturated aqueous $NH_4OH$/ethanol 3/1 (vol/vol) solution for 5 h at 55° C. The supernatant was collected and the CPG beads were washed 3 times with 0.25 mL of EtOH/$CH_3ON$/$H_2O$ 3/1/1 (vol). The solutions were pooled and evaporated (speed vac).

At this point, the crude $^3$LON-$T_{15}$ and $^3$LON-$A_{15}$ behave quite differently. While $^3$LON-$T_{15}$ crude could be readily solubilized in 1 mL milliQ water, a heavy precipitate was obtained from $^3$LON-$A_{15}$. $^3$LON-$T_{15}$ was then purified on an analytical $C_4$-reverse phase HPLC using buffer A (0.1 M triethylammonium acetate, pH 7.0, 5% acetonitrile) and buffer B (0.1 M triethylammonium acetate, pH 7.0, 80% acetonitrile): gradient increase from 0 to 80% B in 10 min and then keeping this ratio constant up to 50 min. The LON eluted after ca. 42 min under these conditions. Fractions containing the LON were pooled and evaporated to dryness. The LON was dissolved in water and dried again two times to remove all residual traces of buffer. Yield of final $^3$LON-$T_{15}$ was excellent (40%).

$^3$LON-$T_{15}$ Crude mixture (MS): Although the inventors were well aware MALDI-TOF analyses are not quantitative, MS of the crude seems to indicate that the single coupling of the phosphoramidite 4 to the polyT chain on the solid support worked well (the peaks at 4504 (M+H)$^+$, 4524 (M+Na)$^+$ and 4542 (M+K)$^+$ correspond to unmodified $dT_{15}$).

Example 3

In this example, LONs were investigated for their ability to self assemble and load Paclitaxel. In order to optimize the inclusion of the lipophilic Paclitaxel, LONs were synthesized with either 2 or 3 hydrocarbon chains attached at their respective 5' end (FIG. 1). The inventors showed that LON based micelles, which are efficient host for hydrophobic drugs like Paclitaxel, can provide stimuli-responsive drug-carriers sensitive to the presence of a complementary oligonucleotide.

Materials and Methods

1. Synthesis of the Triple Chain Phosphoramidite 4

Phosphoramidite 4 was synthesized as described in Example 1. Of note, MALDI-MS of the very lipophilic 2,2,2-tris-stearyl acetic acid 3 required the use of a DCTB matrix (trans-2-[3-(4-tert-butylphenyl)-2-methyl-2-propenylidene]malononitrile) doped with Ag$^+$ (or Na$^+$).

Procedure: this analysis was performed by the CESAMO (Bordeaux, France) on a Voyager mass spectrometer (Applied Biosystems). The instrument is equipped with a pulsed N$_2$ laser (337 nm) and a time-delayed extracted ion source. Spectra were recorded in the positive-ion mode using the reflectron and with an accelerating voltage of 20 kV. Samples were dissolved in CH$_2$Cl$_2$ at 10 mg/ml. The DCTB matrix solution was prepared by dissolving 10 mg in 1 ml of CH$_2$Cl$_2$. A solution of cationisation agent (AgTFA, 10 mg/ml) was also prepared. The solutions were combined in a 10:1:1 volume ratio of matrix to sample to cationisation agent. One to two microliters of the obtained solution was deposited onto the sample target and vacuum-dried.

2. LON Synthesis and MS

LONs were synthesized using the phosphoramidite methodology on an automated Expedite 8909 DNA synthesizer at the μmole scale on 500 Å primer support (loading: 60-100 μmol/g, Link technologies, Synbase Control Pore Glass). The elongation of the oligonucleotide can be achieved following both a 3' to 5' and 5' to 3' elongation procedures. Accordingly, the nucleolipid modified phosphoramidite is inserted at the last position (either 5' or 3', depending on the elongation procedure selected). Autoclaved milliQ water was used whenever water was required for the handling of oligonucleotides or LONs.

Mass spectra measurements were performed on a MALDI-Tof-ToF mass spectrometer (Ultraflex, Bruker Daltonics, Bremen, Germany). Best results were obtained in the linear mode with positive-ion detection. Mass spectra were acquired with an ion source voltage 1 of 25 kV, an ion source voltage 2 of 23.5 kV, a lens voltage of 6 kV, by accumulating the ion signals from 1000 laser shots at constant laser fluence with a 100 Hz laser. External mass calibration was achieved using a mixture of oligonucleotides $dT_{12}$-$dT_{18}$ (Sigma).

1:1 mixture of samples of LONs (~20-50 μM) and matrix was spotted on a MALDI target and air-dried before analysis.

The performance of the following matrices was evaluated: 2,5-dihydroxybenzoic acid (DHB), 2,4,6-trihydroxy-acetophenone (THAP), 3-hydroxypicolinic acid (3-HPA) and 2,6-dihydroxyacetophenone (DHA). THAP at a concentration of 20 mg/mL in a 4:1 mixture of ethanol and 100 mM aqueous ammonium citrate was shown to yield optimal mass spectral results.

3. Transmission and Scanning Electron Microscopy (TEM and SEM)

Transmission Electron Microscopy (TEM). Samples were imaged by negative staining microscopy with a Hitachi H 7650 electron microscope. Samples containing LONs (concentrations and mean sizes are indicated in TEM images) were transferred to a carbon-coated copper grid for ten minutes. The sample was then dried and stained with 2.5% (W/W) of uranyl acetate in water for five minutes.

Scanning Electron Microscopy (SEM). Samples were examined at an accelerating voltage of 10 kV. Typically 20 ml of sample containing the LON aggregates were dried spread on polished stainless steel platelets and then coated with a 6-10 nm layer of gold-palladium alloy under vacuum with a sputter Coater Balzers SCD050. Observations were made with a Philips XL30S FEG instrument.

4. Solubilization of Paclitaxel in Aqueous Solutions of LONs

Representative example: Paclitaxel solubilization by a mixture of $dA_{15}$ and $^3$LON $T_{15}$ oligonucleotides.

Preparation of the Samples. For the experiments of LON-assisted dissolution of Paclitaxel, 40 nmol of $dA_{15}$ and $^3$LON-$T_{15}$ were dried (speedvac). 0.2 mL PBS (10 mM phosphate buffer pH 7+100 mM of NaCl) were then added and the mixture vortexed.

The obtained aqueous solution was added to a test tube containing 0.6 mg of thoroughly dried Paclitaxel. Vortexing and then sonication at 30° C. for 30 min produced turbid colloidal suspensions (pure buffer solutions gave clear solutions above the Paclitaxel precipitate). Subsequent centrifugation (2000 rpm; 20 min) followed by filtration through a 450 nm filter gave the sample ready for HPLC analysis.

Determination of Paclitaxel Concentrations. The concentrations of Paclitaxel in the different aqueous solutions were measured by reverse phase HPLC (Macherey Nagel EC 250/4 Nucleosil 120-5 C4) with detection at 227 nm. Elution conditions (eluent A (V/V): 5% CH$_3$CN/95% 0.1 M TEAA pH 7; eluent B: 80% CH$_3$CN/20% 0.1 M TEAA pH 7): isochratic (16% of B) for 2 min, 16->90% of B after 28 min and back to 16% of B.

The Paclitaxel concentrations were estimated by measuring the area of the Paclitaxel peak in the chromatogram after injection of a fixed volume (45 μL) of the solution. The latter was translated into a Paclitaxel concentration using a calibration curve. The concentrations tested for the calibration curve spanned the range of Paclitaxel concentrations obtained in the Paclitaxel-loading experiments.

Results and Discussion

1. Chemistry of LONs

LONS were efficiently synthesized using the classical phosphoramidite chemistry for oligonucleotides.

The synthesis of the triple hydrocarbon chain modifier is illustrated in Scheme 1 starting from diethyl malonate and stearyl bromide.

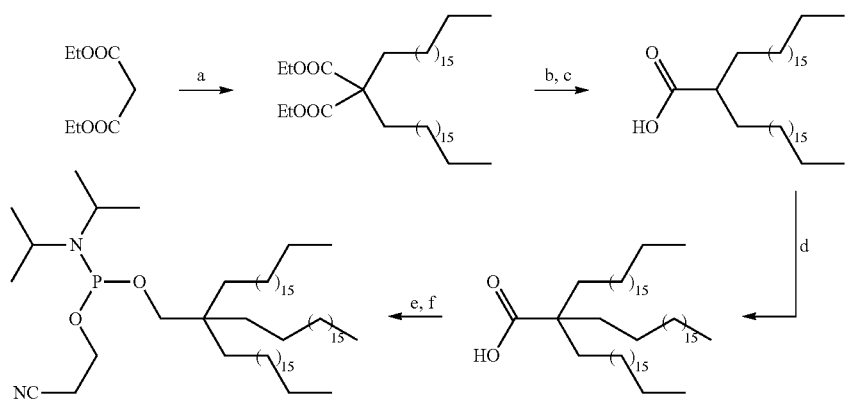

Malonic ester synthesis first afforded the bis-stearyl adduct 1, which was further hydrolyzed and decarboxylated to the monoacid 2. The latter was then alkylated with stearyl bromide after deprotonation with an excess of LDA to give the triple chain monoacid 3. Of note and probably because of its high lipophilicity, 3 proved quite reluctant to traditional mass analysis (ESI and maldi using conventional organic matrices). Mass analysis (maldi) of this compound required the use of a DCTB matrix (trans-2-[3-(4-tert-butylphenyl)-2-methyl-2-propenylidene]malononitrile) doped with $Ag^+$ or $Na^+$. Reduction with LAH followed by phosphitylation of the resulting alcohol afforded the target phosphoramidite 4 ready for the automated, solid supported synthesis of oligonucleotides. Oligonucleotides $dT_{15}$ and $dA_{15}$ were derivatized with these 2 phosphoramidites (FIG. 1). The coupling efficiency of the new phosphoramidite 4 to the elongating oligonucleotide sequence could not be directly determined due to the absence of the DMT protecting group in this phosphoramidite. Nevertheless, the coupling yield was good as estimated by the integration of the mass spectrum signals from the crude reaction mixture of $^3LON-T_{15}$ and the excellent 40% final yield of the HPLC-purified LON. The oligonucleotide sequences $dA_{15}$ (adenine 15-mer) and $dT_{15}$ (thymidine 15-mer) were appended to these lipophilic modifiers to probe the influence of the oligonucleotide sequence. This resulted in the synthesis of four different LONs (FIG. 1).

2. Physicochemical Properties of LONs.

As true surfactants, LONs can self assemble in aqueous media. Both the lipophilic segment and the oligonucleotide sequence were found to markedly influence the aggregation behavior of the LONs of the invention. Overall and not surprisingly, adenosine-containing LONs ($^3LON-A_{15}$) were less soluble in water than their thymidine counterparts ($^3LON-T_{15}$). Interestingly, the presence of the triple chain motif resulted in a peculiar behavior of $^3LON-A_{15}$ and $^3LON-T_{15}$. The latter could be HPLC-purified and characterized by MS. Yet, a slow aggregation tendency was observed after storage at −20° C., $^3LON-T_{15}$ being still detectable by MS in the solution. In contrast, immediate and irreversible aggregation of $^3LON-A_{15}$ took place after cleavage and deprotection of the crude LON. The aggregates were so stable that MS detection and purification of $^3LON-A_{15}$ by PAGE or HPLC proved impossible. Consequently, dynamic light scattering, transmission electron microscopy and SEM experiments were carried out with the solutions of one purified LON only. Aqueous samples containing LONs were studied under different conditions including pure water and aqueous suspensions of varying ionic strength and temperature (25-45° C.). All the LONs investigated, namely $^3LON-T_{15}$, yielded small spherical objects ranging from approximately 8 to 20 nm in diameter as characterized by DLS, transmission and scanning electronic microscopies (TEM and SEM). For example, TEM and SEM imaging of $^3LON-T_{15}$ samples dissolved in pure water shows micellar aggregates. The micellar architecture of these assemblies can be explained based upon the molecular dimensions of 15 nucleobase-long LONs. Indeed, such molecules are flexible, with cone shape structure and dimensions compatible with the self-aggregation into spherical micelles. The DLS study of $^3LON-T_{15}$ in water indicates that the size of aggregates is poorly sensitive to ionic strength. Likewise, the size of aggregates is poorly affected by temperature in the 25-45° C. range or the concentration of the amphiphile.

3. Drug Loading Experiments.

Figure 3:
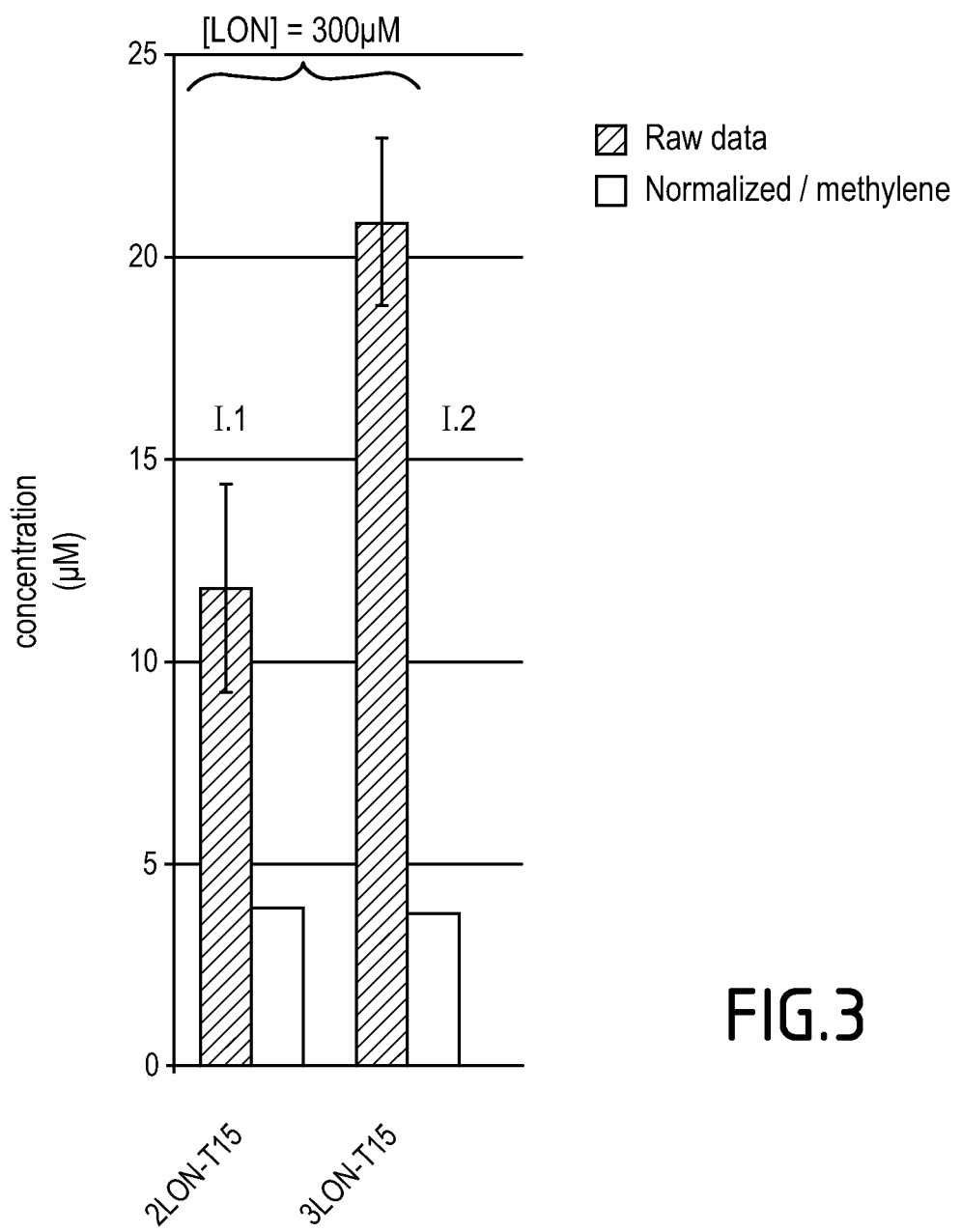
FIG. 3 shows LON-assisted aqueous solubilization of Paclitaxel in 1 mM phosphate buffer and 100 mM NaCl.

Physicochemical experiments and microscopy observations demonstrated that LONs self-associate into micelle-like aggregates. The inventors hypothesized that the hydrophobic core of LON aggregates could promote the solubilization in aqueous environments of hydrophobic drugs like Paclitaxel. To this end, the LONs were solubilized (200 or 300 µM solutions) in 10 mM PBS buffer at pH 7 and 100 mM NaCl. The LON aqueous solutions were bath-sonicated and heated in the presence of a thin film of Paclitaxel and the resulting suspensions filtered through a 0.4 µm pore to remove non-incorporated Paclitaxel aggregates. The Paclitaxel concentrations still remaining in solution were then determined by $RP-C_4$-HPLC (FIG. 3). For a given oligonucleotide sequence, this seems to indicate that the solubility of Paclitaxel is proportional to the number of carbon atoms present in the hydrocarbon chains of LONs. On the other hand, the oligonucleotide sequence was quite unexpectedly found to be of prime importance.

4. Discussion.

What drives the release of the drug loaded in the hydrophobic core of the aggregates upon DNA annealing is not obvious at first sight. It must first be noticed that the nature of the LON aggregates is not changed upon binding the cDNA and micellar aggregates are still observed in the presence of the cDNA. Yet, contraction of the core micelle is observed following hybridization of the complementary $dA_{15}$ with $^3LON-T_{15}$ aggegates. Such contraction of the micellar core is not observed with the ncDNA. These results are quite unexpected. Formation of the rather long and stiff rod-shaped dsDNA is indeed expected to increase the size of the micelle compared to the quite flexible ss-DNA segment of LONs. Consequently, the present DLS results strongly suggest that the micellar hydrophobic core experience much contraction upon DNA duplex formation. This observation may shed light on the mechanism of the triggered release of Paclitaxel from LON micelles. In fact, the ss-DNA polar heads of LONs may experience conformational freedom in the aqueous phase within the LON aggregates. The surface area occupied by each polar head of ss-LONs may be quite large. Consequently, the LON alkyl chains may be poorly packed within the hydrophobic core thus leaving room for hosting hydrophobic guests. In the contrary, the stiffness and the rather small cross section of DNA double helices might allow for a better compaction of the alkyl chains within the core of the micelle with the concomitant release of part of the loaded Paclitaxel molecules.

Conclusions

In this study the inventors present the synthesis of LONs featuring triple lipophilic chains. These LONs self-assemble into micelles, which are prone to host Paclitaxel molecules within their hydrophobic cores. These results demonstrate that the composition of the LONs both in terms of the lipid and the oligonucleotide sequence impact their ability to host lipophilic molecules. Overall, the polynucleotide sequence serves three roles: (1) it promotes the transfer of the alkyl chains of the LONs into water, (2) it potentializes the drug intake of the LON aggregates and (3) it can hybridize with the cDNA sequence to trigger the release of the drug.

Numerous stimuli-bioresponsive drug delivery systems have been developed to induce the release of the drug in response to certain stimuli like pH, temperature, redox potential, enzymes, light, and ultrasound. In this contribution the inventors demonstrate that the drug loading of LON based nanomaterials can be modulated via complementary oligonucleotide stimulus. LON aggregates afford an original and specific stimuli-bioresponsive alternative to address the drug controlled delivery issue.

Example 4

$^3$LASO#15: DNA of sequence SEQ ID NO: 6 with a phosphodiester backbone bearing a triple alkyl chain at its 5' end (C18)$_3$CCH$_2$—O—P(=O)(—O[-1])-O-5'-AAC TTG TTT CCT GCA GGT GA-3'-OH This example describes the production of a lipid conjugated antisense oligonucleotide (LASO) featuring the ASO#15 sequence and a triple chain inserted at the 5' extremity.

Prior to use, the phosphoramidite 4 was dried over P$_2$O$_5$ overnight. It was then dissolved in dry CH$_2$Cl$_2$/CH$_3$CN 3/1 to a 0.1 M concentration. N-benzylthiotetrazole was used for activation of phosphoramidite prior to coupling. The phosphoramidite 4 (200 mL, 0.1 M sol.) was manually coupled last on the solid support with the activator and the phosphoramidite (0.25 mL) for 5 min. Deblocking and detachment from the solid support was achieved using 1 mL of a saturated aqueous NH$_4$OH/ethanol 3/1 (vol/vol) solution for 5 h at 55° C. The supernatant was collected and the CPG beads were washed 3 times with 0.25 mL of EtOH/CH$_3$CN/H$_2$O 3/1/1 (vol). The solutions were pooled and evaporated (speed vac).

At this point, the crude $^3$LASO#15 was then purified on an analytical C$_4$-reverse phase HPLC using buffer A (0.1 M triethylammonium acetate, pH 7.0, 5% acetonitrile) and buffer B (0.1 M triethylammonium acetate, pH 7.0, 80% acetonitrile): gradient increase from 0 to 80% B in 10 min and then keeping this ratio constant up to 50 min.

MALDI-TOP mass-analyses: $^3$LASO#15: [M+H]+ found: 6985 Da.

Example 5

This example shows that the modified oligonucleotides according to the invention are capable of inhibiting TCTP expression.

Materials and Methods

Oligonucleotides
  Different Modified Oligonucleotides were Used:
  LASO#15: DNA of sequence SEQ ID NO: 6 with a phosphodiester backbone bearing a triple alkyl chain at its 5' end;
  LASO#Scr: DNA of sequence SEQ ID NO: 4 with a phosphodiester backbone bearing a triple alkyl chain at its 5' end.

Cell Lines and Cell Culture Conditions

The CR prostate cancer cell line PC-3 was purchased from the American Type Culture Collection (Rockville, Md., USA). The cells were maintained in Dulbecco's Modified Eagle's Medium (Invitrogen, Cergy Pontoise, France), supplemented with 10% fetal calf serum (FCS).

Transfections

Lipid-conjugated oligonucleotide, LASO#15 was tested on TCTP protein expression using western-blot (LASO#Scr was used as negative control).

Prostatic cell line were transfected with LASO#15 at various concentrations (from 30 nM to 100 nM), in OptiMEM® medium (Invitrogen), without serum and in the absence of Oligofectamine™ transfection reagent (Invitrogen).

Serum was added 4 hours after transfection. Two or three days after transfection, the level of TCTP protein expression and GAPDH (used as housekeeping gene) were determined by performing western blotting, and the in vitro growth inhibitory effects of LASO#15 on PC-3 cells were assessed using an MTT assay.

Western Blot Analysis

Western Blot analysis was performed as described previously (Rocchi et al., 2004, Cancer Res. 64:6595-602) with 1:2000 rabbit TCTP polyclonal antibody (Abcam Inc., Cambridge, UK). Loading levels were normalized using 1:5000 rabbit anti-glyceraldehyde-3-phosphate dehydrogenase polyclonal (Abcam Inc.).

MTT Assay

The MTT assay was performed as described previously (Rocchi et al., 2004, Cancer Res. 64:6595-602).

Results

Figure 4:
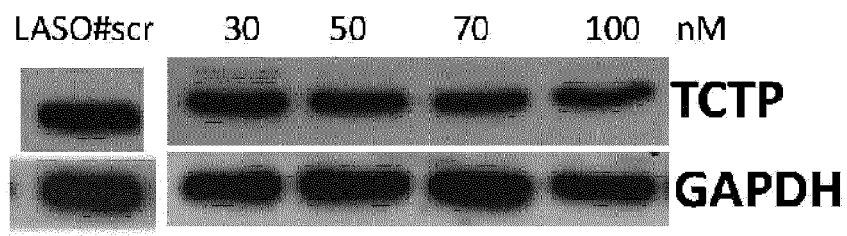
FIG. 4 shows TCTP and GAPDH protein expression, 3 days after transfection, in prostatic cells transfected, in the absence of Oligofectamine, with TCTP LASO#15 or with scramble LASO#Scr serving as negative control.
Figure 5:
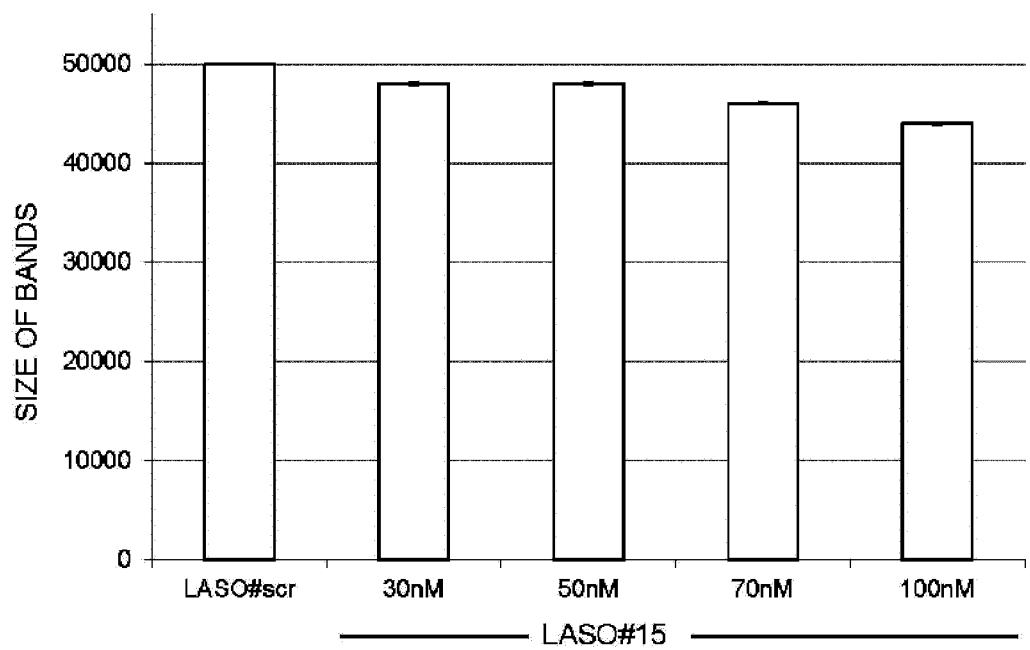
FIG. 5 shows histograms representing the level of the sizes of bands of the Western Blot of FIG. 4.

As shown in FIGS. 4 and 5, the inventors demonstrated that the addition of a triple alkyle chain on the 5' part of the antisense oligonucleotide enables inhibiting specifically TCTP protein, even in the absence of the Oligofectamine™ transfection agent, in particular when the antisense oligonucleotide was used at a concentration of 100 nM.

Figure 6:
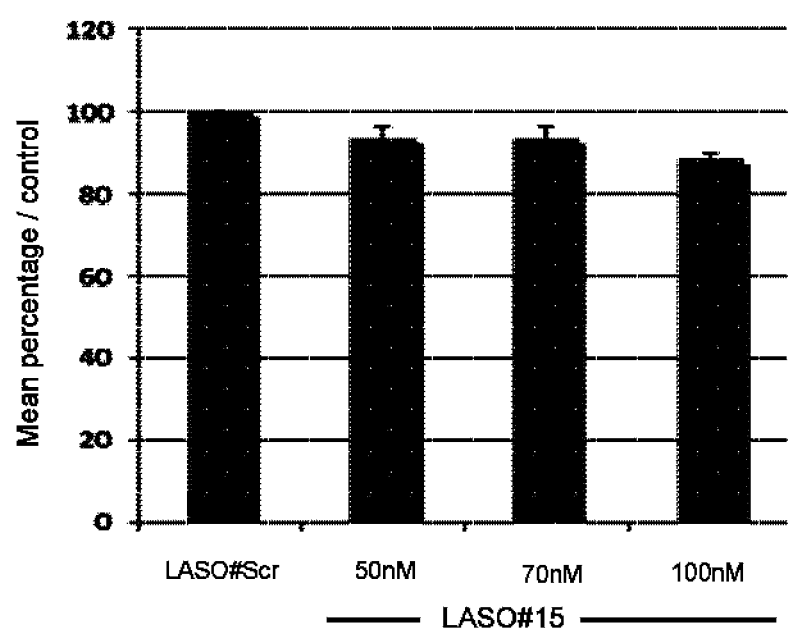
FIG. 6 histograms representing the mean percentage of viable PC-3 prostatic cells, determined by MTT assay, after transfection, in the absence of Oligofectamine, with TCTP LASO#15 or with scramble LASO#Scr serving as negative control.

The inventors also observed that the specific inhibition of TCTP protein with LASO#15 enabled inhibiting the growth of the PC-3 cells (see FIG. 6).

The invention claimed is:

1. An oligonucleotide modified by substitution at the 3' or the 5' end by a moiety comprising at least three saturated or unsaturated, linear or branched hydrocarbon chains comprising from 2 to 30 carbon atoms.

2. The modified oligonucleotide according to claim 1, of the general formula (I):

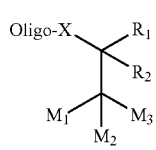

wherein:

Oligo represents an oligonucleotide sequence which may be oriented 3'-5' or 5'-3', simple and/or double stranded, Deoxyribonucleic Acid (DNA), Ribonucleic acide (RNA), and/or comprise modified nucleotides selected from the group consisting of locked nucleic acid (LNA), 2'-OMe analogs, 2'-phosphorothioate analogs, 2'-fluoro analogs, 2'-Cl analogs, 2'-Br analogs, 2'-CN analogs, 2'-$CF_3$ analogs, 2'-$OCF_3$ analogs, 2'-OCN analogs, 2'-O-alkyl analogs, 2'-S-alkyl analogs, 2'-N-alkyl analogs, 2'-O-alkenyl analogs, 2'-S-alkenyl analogs, 2'-N-alkenyl analogs, 2'-$SOCH_3$ analogs, 2'-$SO_2CH_3$ analogs, 2'-$ONO_2$ analogs, 2'-$NO_2$ analogs, 2'-$N_3$ analogs, 2'-$NH_2$, analogs and combinations thereof;

X represents a divalent linker moiety selected from ether —O—, thio —S—, amino —NH—, and methylene —$CH_2$—;

$R_1$ and $R_2$ may be identical or different and represent:
(i) a hydrogen atom,
(ii) a halogen,
(iii) a hydroxyl group,
(iv) an alkyl group comprising from 1 to 12 carbon atoms;

$M_1$, $M_2$ and $M_3$ may be identical or different and represent:
a saturated or unsaturated, linear or branched hydrocarbon chain comprising from 2 to 30 carbon atoms, which may be substituted by one or more halogen atoms, and/or be interrupted by one or more groups selected from ether —O—, thio —S—, amino —NH—, oxycarbonyl —O—C(O)—, thiocarbamate —O—C(S)—NH—, carbonate —O—C(O)—O—, carbamate —O—C(O)—NH—, phosphate —O—P(O)(O)—O— and phosphonate —P—O(O)(O)— groups; and/or be substituted at the terminal carbon atom by an aliphatic or aromatic;
an acyl radical with 2 to 30 carbon atoms, or
an acylglycerol, sphingosine or ceramide group.

3. The modified oligonucleotide according to claim 2, wherein the modified nucleotides are selected from the group consisting of LNA, 2'-OMe analogs, 2'-phosphorothioate analogs and 2'-fluoro analogs.

4. The modified oligonucleotide according to claim 1, wherein the oligonucleotide is selected from the group consisting of $dT_{15}$, $dA_{15}$ and an oligonucleotide consisting of the sequence SEQ ID NO: 6.

5. The modified oligonucleotide according to claim 2, wherein the divalent linker moiety is ether —O—.

6. The modified oligonucleotide according to claim 2, wherein $R_1$ and $R_2$ are hydrogen atoms.

7. The modified oligonucleotide according to claim 2, wherein $M_1$, $M_2$ and $M_3$ represent a hydrocarbon chain comprising from 6 to 22 carbon atoms.

8. The modified oligonucleotide according to claim 1, wherein the oligonucleotide comprises a fragment of at least 10 consecutive nucleotides of a sequence selected from the group consisting of SEQ ID NO: 2 (5'-ACCAATGAGC-GAGTCATCAA-3'), SEQ ID NO: 3 (5'-AACCCGUCCGC-GAUCUCCCGG-3'), SEQ ID NO: 6 (5'-AACTTGTTTC-CTGCAGGTGA-3'), SEQ ID NO: 7 (5'-TGGTTCATGACAATATCGAC-3'), SEQ ID NO: 8 (5'-TAATCATGATGGCGACTGAA-3'), SEQ ID NO: 16 (5'-ACCAGTGATTACTGTGCTTT-3'), SEQ ID NO: 17 (5'-CTTGTAGGCTTCTTTTGTGA-3'), SEQ ID NO: 18 (5'-ATGTAATCTTTGATGTACTT-3'), SEQ ID NO: 19 (5'-GTTTCCCTTTGATTGATTTC-3'), SEQ ID NO: 20 (5'-TTCTGGTCTCTGTTCTTCAA-3'), SEQ ID NO: 25 (5'-AGAAAATCATATATGGGGTC-3'), SEQ ID NO: 27 (5'-TTAACATTTCTCCATTTCTA-3'), SEQ ID NO: 29 (5'-GTCATAAAAGGTTTTACTCT-3') and SEQ ID NO: 31 (5'-GAAATTAGCAAGGATGTGCT-3').

9. The modified oligonucleotide according to claim 1, wherein the oligonucleotide comprises or consists of a sequence selected from the group consisting of SEQ ID NO: 2, SEQ ID NO: 6 and SEQ ID NO: 7.

10. A process of manufacture of a modified oligonucleotide according to claim 1, comprising the steps of:
(i) synthesizing the oligonucleotide;
(ii) modifying the oligonucleotide by reaction with a suitable reactant comprising a moiety having at least three saturated or unsaturated, linear or branched hydrocarbon chains comprising from 2 to 30 carbon atoms;
(iii) recovering the modified oligonucleotide.

11. A medicament comprising a modified antisense oligonucleotide as defined in claim 1.

12. A method for treating cancer, comprising the administration to a patient in need thereof of a pharmaceutically acceptable amount of a modified antisense oligonucleotide according to claim 1.

13. The method of claim 12, wherein the cancer is selected from the group consisting of prostate cancer, colon cancer, colorectal cancer, breast cancer, liver cancer, erythroleukemia, gliomas, melanomas, hepatoblastomas and lymphomas.

14. The method of claim 12, wherein the cancer is a prostate cancer.

15. An aqueous composition comprising modified oligonucleotides according to claim 1, wherein the modified oligonucleotides self-assembled into micelles and optionally comprising a hydrophobic active principle hosted in said micelles, said hydrophobic active principle being preferably selected from the group consisting of Paclitaxel, Docetaxel, Vincristine, Vinorelbine, and Abraxane; Tamoxifen, Gonadotrophin-releasing hormone (GnRH) agonists and antagonists, androgen receptor (AR) antagonist, and estrogen receptor (ER) antagonists; Cyclophosphamide, Chlorambucil and Melphalan; Methotrexate, Cytarabine, Fludarabine, 6-Mercaptopurine and 5-Fluorouracil; Doxorubicin, Irinotecan, Platinum derivatives, Cisplatin, Carboplatin, Oxaliplatin; Bicalutamide, Anastrozole, Examestane and Letrozole; Imatinib (Gleevec), Gefitinib and Erlotinib; Rituximab, Trastuzumab (Herceptin) and Gemtuzumab ozogamicin; Interferon-alpha; Tretinoin and Arsenic trioxide; Bevicizumab, Serafinib and Sunitinib.

16. The aqueous composition according to claim 13 as a vehicle.

17. The aqueous composition according to claim 16, as a vehicle of a sparingly hydrosoluble active principle, wherein the active principle is selected from the group consisting of Paclitaxel, Docetaxel, Vincristine, Vinorelbine, and Abraxane; Tamoxifen, Gonadotrophin-releasing hormone (GnRH) agonists and antagonists, androgen receptor (AR) antagonist, and estrogen receptor (ER) antagonists; Cyclophosphamide, Chlorambucil and Melphalan; Methotrexate, Cytarabine, Fludarabine, 6-Mercaptopurine and 5-Fluorouracil; Doxorubicin, Irinotecan, Platinum derivatives, Cisplatin, Carboplatin, Oxaliplatin; Bicalutamide, Anastrozole, Examestane and Letrozole; Imatinib (Gleevec), Gefitinib and Erlotinib; Rituximab, Trastuzumab (Herceptin) and Gemtuzumab ozogamicin; Interferon-alpha; Tretinoin and Arsenic trioxide; Bevicizumab, Serafinib and Sunitinib.

18. A medicament comprising the aqueous composition as defined in claim 15.

19. A method for treating cancer, comprising the administration to a patient in need thereof of a pharmaceutically acceptable amount of the aqueous composition according to claim 15.

* * * * *